United States Patent
Khatib

(10) Patent No.: US 11,155,870 B2
(45) Date of Patent: Oct. 26, 2021

(54) METHODS AND COMPOSITIONS FOR MONITORING AND ENHANCING EARLY EMBRYO DEVELOPMENT

(71) Applicant: Wisconsin Alumni Research Foundation, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/371,147

(22) Filed: Apr. 1, 2019

(65) Prior Publication Data

US 2019/0218610 A1 Jul. 18, 2019

Related U.S. Application Data

(63) Continuation of application No. 14/156,403, filed on Jan. 15, 2014, now abandoned.

(60) Provisional application No. 61/752,969, filed on Jan. 15, 2013.

(51) Int. Cl.
*C12Q 1/6876* (2018.01)
*C12N 15/113* (2010.01)

(52) U.S. Cl.
CPC ........ *C12Q 1/6876* (2013.01); *C12N 15/1135* (2013.01); *C12N 2310/14* (2013.01); *C12Q 2600/124* (2013.01); *C12Q 2600/158* (2013.01)

(58) Field of Classification Search
CPC .......................... C12Q 1/6876; C12N 2310/14
USPC ......................................................... 435/325
See application file for complete search history.

(56) References Cited

PUBLICATIONS

Tesfaye (2004, Reproduction in Domestic Animals, 39:396-404).*
Lonergan (Theriogenology, 2008, 69:17-22.*
Wrenzycki (2005, Reproduction and Development, 17:23-35).*
Lonergan, Theriogenology, 2006, 65:137-152).*

* cited by examiner

*Primary Examiner* — Valarie E Bertoglio
(74) *Attorney, Agent, or Firm* — Boyle Frederickson S.C.

(57) ABSTRACT

Method for determining developmental fate of early embryos comprises measuring the expression level of a gene selected from the group consisting of CDKN1C, IGF2R, MAGEL2, MKRN3, NAP1L5, NDN, PEG3, PHLDA2, TSSC4, and UBE3A genes. Also disclosed is a method for improving pregnancy rate, wherein early embryos whose expression level of the MKRN3, NDN, PEG3, PHLDA2, TSSC4, or UBE3A gene is not increased, or the expression level of the CDKN1C, IGF2R, MAGEL2, or NAP1L5 gene is not decreased, are selected for planting into a suitable uterus for further development. Also disclosed are methods for increasing the likelihood of an early embryo to develop successfully into full-term pregnancy, wherein a suitable amount of siRNA corresponding to the PHLDA2 gene is injected into a fertilized egg which is in turn cultured further and planted into a suitable uterus.

3 Claims, 7 Drawing Sheets

Specification includes a Sequence Listing.

SEQUENCE LISTING

<160> NUMBER OF SEQ ID NOS: 44

<210> SEQ ID NO 1
<211> LENGTH: 23
<212> TYPE: DNA
<213> ORGANISM: Artificial Sequence
<220> FEATURE:
<223> OTHER INFORMATION: PHLDA2 antisense

<400> SEQUENCE: 1
aguagcaccg ggcuauaucd tdt                                                   23

<210> SEQ ID NO 2
<211> LENGTH: 23
<212> TYPE: DNA
<213> ORGANISM: Artificial Sequence
<220> FEATURE:
<223> OTHER INFORMATION: PHLDA2 Sense

<400> SEQUENCE: 2
gauauagccc ggugcuacud tdt                                                   23

<210> SEQ ID NO 3
<211> LENGTH: 23
<212> TYPE: DNA
<213> ORGANISM: Artificial Sequence
<220> FEATURE:
<223> OTHER INFORMATION: CDKN1C antisense

<400> SEQUENCE: 3
aaaucccuga gugcggcggd tdt                                                   23

<210> SEQ ID NO 4
<211> LENGTH: 23
<212> TYPE: DNA
<213> ORGANISM: Artificial Sequence
<220> FEATURE:
<223> OTHER INFORMATION: CDKN1C sense

<400> SEQUENCE: 4
ccgccgcacu cagggauuud tdt                                                   23

<210> SEQ ID NO 5
<211> LENGTH: 21
<212> TYPE: DNA
<213> ORGANISM: Artificial Sequence
<220> FEATURE:
<223> OTHER INFORMATION: UBE3A-F

<400> SEQUENCE: 5
gggactctgt tgtgattagg g                                                     21

<210> SEQ ID NO 6
<211> LENGTH: 22
<212> TYPE: DNA
<213> ORGANISM: Artificial Sequence
<220> FEATURE:
<223> OTHER INFORMATION: UBE3A-R

<400> SEQUENCE: 6
taggtaacct ttctgtgtct gg                                                    22

<210> SEQ ID NO 7
<211> LENGTH: 18
<212> TYPE: DNA
<213> ORGANISM: Artificial Sequence

```
<220> FEATURE:
<223> OTHER INFORMATION: NDNa-F

<400> SEQUENCE: 7
aacgtgctgc gcatcttg                                                  18

<210> SEQ ID NO 8
<211> LENGTH: 22
<212> TYPE: DNA
<213> ORGANISM: Artificial Sequence
<220> FEATURE:
<223> OTHER INFORMATION: NDNa-R

<400> SEQUENCE: 8
tcaggtagtt ctgctggacg aa                                             22

<210> SEQ ID NO 9
<211> LENGTH: 20
<212> TYPE: DNA
<213> ORGANISM: Artificial Sequence
<220> FEATURE:
<223> OTHER INFORMATION: MAGEL2b-F

<400> SEQUENCE: 9
ctgatggtgg ttctgagcct                                                20

<210> SEQ ID NO 10
<211> LENGTH: 20
<212> TYPE: DNA
<213> ORGANISM: Artificial Sequence
<220> FEATURE:
<223> OTHER INFORMATION: MAGEL2b-R

<400> SEQUENCE: 10
caggacaatc atcttgctgg                                                20

<210> SEQ ID NO 11
<211> LENGTH: 20
<212> TYPE: DNA
<213> ORGANISM: Artificial Sequence
<220> FEATURE:
<223> OTHER INFORMATION: MKRN3-F

<400> SEQUENCE: 11
ctgcagacag cggccctagc                                                20

<210> SEQ ID NO 12
<211> LENGTH: 20
<212> TYPE: DNA
<213> ORGANISM: Artificial Sequence
<220> FEATURE:
<223> OTHER INFORMATION: MKRN3-R

<400> SEQUENCE: 12
cccggtaggg ttgcccagga                                                20

<210> SEQ ID NO 13
<211> LENGTH: 19
<212> TYPE: DNA
<213> ORGANISM: Artificial Sequence
<220> FEATURE:
<223> OTHER INFORMATION: CDKN1C-F

<400> SEQUENCE: 13
caagcggctg cgatgagag                                                 19
```

```
<210> SEQ ID NO 14
<211> LENGTH: 19
<212> TYPE: DNA
<213> ORGANISM: Artificial Sequence
<220> FEATURE:
<223> OTHER INFORMATION: CDKN1C-R

<400> SEQUENCE: 14
tcctgtccac tgcccaacg                                                  19

<210> SEQ ID NO 15
<211> LENGTH: 19
<212> TYPE: DNA
<213> ORGANISM: Artificial Sequence
<220> FEATURE:
<223> OTHER INFORMATION: IGF2R-F

<400> SEQUENCE: 15
cagtcgcaaa gtcggaacc                                                  19

<210> SEQ ID NO 16
<211> LENGTH: 21
<212> TYPE: DNA
<213> ORGANISM: Artificial Sequence
<220> FEATURE:
<223> OTHER INFORMATION: IGF2R-R

<400> SEQUENCE: 16
ggtcacagtg gaagaagatg g                                               21

<210> SEQ ID NO 17
<211> LENGTH: 18
<212> TYPE: DNA
<213> ORGANISM: Artificial Sequence
<220> FEATURE:
<223> OTHER INFORMATION: PEG3c-F

<400> SEQUENCE: 17
cgccaaagtc agggagag                                                   18

<210> SEQ ID NO 18
<211> LENGTH: 18
<212> TYPE: DNA
<213> ORGANISM: Artificial Sequence
<220> FEATURE:
<223> OTHER INFORMATION: PEG3c-R

<400> SEQUENCE: 18
cttaactgcc aggacacc                                                   18

<210> SEQ ID NO 19
<211> LENGTH: 20
<212> TYPE: DNA
<213> ORGANISM: Artificial Sequence
<220> FEATURE:
<223> OTHER INFORMATION: NAP1L5-F

<400> SEQUENCE: 19
tcctttcgtc acagtatcgc                                                 20

<210> SEQ ID NO 20
<211> LENGTH: 18
<212> TYPE: DNA
<213> ORGANISM: Artificial Sequence
<220> FEATURE:
<223> OTHER INFORMATION: NAP1L5-R
```

<400> SEQUENCE: 20
tgagttctgc tgctgctg                                                    18

<210> SEQ ID NO 21
<211> LENGTH: 18
<212> TYPE: DNA
<213> ORGANISM: Artificial Sequence
<220> FEATURE:
<223> OTHER INFORMATION: TSSC4-F

<400> SEQUENCE: 21
tgccaccaag aaccttcg                                                    18

<210> SEQ ID NO 22
<211> LENGTH: 18
<212> TYPE: DNA
<213> ORGANISM: Artificial Sequence
<220> FEATURE:
<223> OTHER INFORMATION: TSSC4-R

<400> SEQUENCE: 22
cctctgccat gtgtcacc                                                    18

<210> SEQ ID NO 23
<211> LENGTH: 19
<212> TYPE: DNA
<213> ORGANISM: Artificial Sequence
<220> FEATURE:
<223> OTHER INFORMATION: PEG10-F

<400> SEQUENCE: 23
ctttccagcc ttcgcagag                                                   19

<210> SEQ ID NO 24
<211> LENGTH: 20
<212> TYPE: DNA
<213> ORGANISM: Artificial Sequence
<220> FEATURE:
<223> OTHER INFORMATION: PEG10-R

<400> SEQUENCE: 24
cttcactcct gtggcaatgg                                                  20

<210> SEQ ID NO 25
<211> LENGTH: 22
<212> TYPE: DNA
<213> ORGANISM: Artificial Sequence
<220> FEATURE:
<223> OTHER INFORMATION: USP29-F

<400> SEQUENCE: 25
aggaggaagt tccctttgtt gc                                               22

<210> SEQ ID NO 26
<211> LENGTH: 22
<212> TYPE: DNA
<213> ORGANISM: Artificial Sequence
<220> FEATURE:
<223> OTHER INFORMATION: USP29-R

<400> SEQUENCE: 26
tctctgtgac ggctgaaata gc                                               22

<210> SEQ ID NO 27
<211> LENGTH: 20
<212> TYPE: DNA
<213> ORGANISM: Artificial Sequence
<220> FEATURE:
<223> OTHER INFORMATION: RTL1-F

<400> SEQUENCE: 27
ccctcctcta ccaccccaag                                                   20

<210> SEQ ID NO 28
<211> LENGTH: 18
<212> TYPE: DNA
<213> ORGANISM: Artificial Sequence
<220> FEATURE:
<223> OTHER INFORMATION: RTL1-R

<400> SEQUENCE: 28
cttgcccgtc cgcttgtc                                                     18

<210> SEQ ID NO 29
<211> LENGTH: 18
<212> TYPE: DNA
<213> ORGANISM: Artificial Sequence
<220> FEATURE:
<223> OTHER INFORMATION: NNAT-F

<400> SEQUENCE: 29
cacccaccca ccagtctc                                                     18

<210> SEQ ID NO 30
<211> LENGTH: 19
<212> TYPE: DNA
<213> ORGANISM: Artificial Sequence
<220> FEATURE:
<223> OTHER INFORMATION: NNAT-R

<400> SEQUENCE: 30
ttctcgacac cgtgtatgc                                                    19

<210> SEQ ID NO 31
<211> LENGTH: 19
<212> TYPE: DNA
<213> ORGANISM: Artificial Sequence
<220> FEATURE:
<223> OTHER INFORMATION: MIM1-F

<400> SEQUENCE: 31
actcggttgt cagtcacac                                                    19

<210> SEQ ID NO 32
<211> LENGTH: 22
<212> TYPE: DNA
<213> ORGANISM: Artificial Sequence
<220> FEATURE:
<223> OTHER INFORMATION: MIM1-R

<400> SEQUENCE: 32
gaatttccat cgtcttatta gc                                                22

<210> SEQ ID NO 33
<211> LENGTH: 19
<212> TYPE: DNA
<213> ORGANISM: Artificial Sequence
<220> FEATURE:

<223> OTHER INFORMATION: IGF2-F

<400> SEQUENCE: 33
tgctgctatg ctgcttacc                                            19

<210> SEQ ID NO 34
<211> LENGTH: 19
<212> TYPE: DNA
<213> ORGANISM: Artificial Sequence
<220> FEATURE:
<223> OTHER INFORMATION: IGF2-R

<400> SEQUENCE: 34
aacactcttc cacgatgcc                                            19

<210> SEQ ID NO 35
<211> LENGTH: 20
<212> TYPE: DNA
<213> ORGANISM: Artificial Sequence
<220> FEATURE:
<223> OTHER INFORMATION: H19-F

<400> SEQUENCE: 35 cgttcccttta gtctcctgac                                          20

<210> SEQ ID NO 36
<211> LENGTH: 18
<212> TYPE: DNA
<213> ORGANISM: Artificial Sequence
<220> FEATURE:
<223> OTHER INFORMATION: H19-R

<400> SEQUENCE: 36
agtccgtgtt ccaagtcc                                             18

<210> SEQ ID NO 37
<211> LENGTH: 21
<212> TYPE: DNA
<213> ORGANISM: Artificial Sequence
<220> FEATURE:
<223> OTHER INFORMATION: XIST-F

<400> SEQUENCE: 37
ccactgagca acaactctag g                                         21

<210> SEQ ID NO 38
<211> LENGTH: 22
<212> TYPE: DNA
<213> ORGANISM: Artificial Sequence
<220> FEATURE:
<223> OTHER INFORMATION: XIST-R

<400> SEQUENCE: 38
ggcaaatatg aagggaacaa cc                                        22

<210> SEQ ID NO 39
<211> LENGTH: 21
<212> TYPE: DNA
<213> ORGANISM: Artificial Sequence
<220> FEATURE:
<223> OTHER INFORMATION: P.O.-F

<400> SEQUENCE: 39
ccactgagca acaactctag g                                         21

```
<210> SEQ ID NO 40
<211> LENGTH: 22
<212> TYPE: DNA
<213> ORGANISM: Artificial Sequence
<220> FEATURE:
<223> OTHER INFORMATION: P.O.-R

<400> SEQUENCE: 40
ggcaaatatg aagggaacaa cc                                          22

<210> SEQ ID NO 41
<211> LENGTH: 22
<212> TYPE: DNA
<213> ORGANISM: Artificial Sequence
<220> FEATURE:
<223> OTHER INFORMATION: B-ACTIN-F

<400> SEQUENCE: 41
aggccaaccg tgagaagatg ac                                          22

<210> SEQ ID NO 42
<211> LENGTH: 21
<212> TYPE: DNA
<213> ORGANISM: Artificial Sequence
<220> FEATURE:
<223> OTHER INFORMATION: B-ACTIN-R

<400> SEQUENCE: 42
ccagaggcat acagggacag c                                           21

<210> SEQ ID NO 43
<211> LENGTH: 18
<212> TYPE: DNA
<213> ORGANISM: Artificial Sequence
<220> FEATURE:
<223> OTHER INFORMATION: GAPDH-F

<400> SEQUENCE: 43
tgcccagaat atcatccc                                               18

<210> SEQ ID NO 44
<211> LENGTH: 18
<212> TYPE: DNA
<213> ORGANISM: Artificial Sequence
<220> FEATURE:
<223> OTHER INFORMATION: GAPDH-R

<400> SEQUENCE: 44
aggtcagatc cacaacag                                               18
```

METHODS AND COMPOSITIONS FOR MONITORING AND ENHANCING EARLY EMBRYO DEVELOPMENT

PRIORITY INFORMATION

This is a continuation application of U.S. application Ser. No. 14/156,403 filed on Jan. 15, 2014, claiming priority to U.S. Application 61/752,969, filed Jan. 15, 2013, the contents of which are incorporated herein by reference.

STATEMENT REGARDING FEDERALLY SPONSORED RESEARCH

This invention was made with U.S. Government support under 12-CRHF-0-6055 awarded by the USDA/NIFA. The U.S. Government has certain rights in the invention.

FIELD OF THE INVENTION

The present invention relates to compositions and methods for monitoring mammalian embryo development. Specifically, gene expression levels are used as indicators of, and manipulated to improve, early embryo development.

BACKGROUND OF THE INVENTION

In vitro fertilization (IVF) involves combining eggs and sperm outside the body in a laboratory. Once an embryo forms, it is planted in the uterus where it will develop further. Even though IVF is a complex and expensive procedure, it has seen steadily increasing use for the past three decades. In humans, since its introduction in the U.S. in 1981, IVF and other similar techniques have resulted in more than 200,000 babies. In other animals, IVF, along with other assisted reproductive technology (ART) have been instrumental in helping scientists address reproductive problems in several endangered species, such as the Florida panthers, giant pandas, black-footed ferrets, ocelots, clouded leopards, chimpanzees, gorillas, South American bush dogs, Mexican wolves, orangutans, and Mongolian wild horses. IVF has also been widely used in animal breeding, for example in dairy cattle.

One challenge facing IVF techniques is low success rates of early embryonic development and pregnancy. For example, only about 40% of fertilized bovine oocytes reach the blastocyst stage by day 8 of development and of these only 45% result in pregnancy [1]. As such, there is a need to better understand the mechanisms affecting proper embryo development, which will in turn allow the development of tools for identifying embryos that will develop successfully for implanting, and for increasing the rates of successful pregnancy through intervention of the development process, especially in cases of non-human animals. By selecting embryos that possess the optimal genetic profile, the odds of successful in vitro fertilization procedures improve. Considering the costs of IVF, this could result in savings of thousands or tens of thousands of dollars as the procedure may not need to be repeated as often before resulting in a successful pregnancy.

To identify genetic factors affecting fertilization success and embryo quality in dairy cattle, the present inventor has established an IVF system and has been using it for genomic and transcriptomic profiling of bovine embryos [see e.g. 2]. With this controlled in vitro system, DNA variations and aberrant gene expression have been discovered that are associated with fertilization success and embryonic development [2-7]. These findings provide valuable genetic and biological markers for fertility of dairy cattle. Nevertheless, the genetic and molecular mechanisms of differential gene expression are yet to be revealed.

Imprinted genes are of particular interest due to their reported roles in embryonic, placental, and neonatal growth [8]. Evidence for the importance of proper imprinted gene function can be seen in animal model studies where disruption or knockouts of particular imprinted genes have resulted in abnormal progeny or lethality in utero [9, 10]. Imprinted genes have also been implicated in livestock development, as differential expression of these genes has been associated with aborted and abnormally developed bovine clone fetuses [11, 12]. However, there is limited information regarding the role of these genes during the early developmental period.

In bovine, one such imprinted gene is PHLDA2 (pleckstrin homology-like domain, family A, member 2). In a previous study that used microarray expression analysis, the present inventor, by comparing the transcriptomes of developed IVF blastocysts to degenerate embryos, which do not properly complete the transition from morula to blastocyst, has found that PHLDA2 was among a number of genes and pathways that were altered in degenerate embryos [3]. PHLDA2 was significantly up-regulated by more than eight-fold compared to blastocysts [3]. However, there was no definitive evidence that this altered gene expression level was responsible for the development fate of the early.

SUMMARY OF THE INVENTION

By demonstrating that the altered gene expression levels were responsible for embryo degeneration, the present inventor has surprisingly discovered that the altered expression levels of several imprinted genes are useful markers for proper embryo development. Specifically, it is revealed that the expression levels of ten (10) imprinted genes differed between blastocysts (successfully developing embryos) and degenerate embryos (or "degenerates"). For example, PHLDA2 showed a higher expression level in degenerates than in blastocysts, while CDKN1C (p57$^{KIP2}$, a member of the CIP/KIP family of cell-cycle inhibitors that have unique roles in embryogenesis, see e.g. [41]) showed a higher expression level in blastocysts compared to degenerates. Knockdown, using gene-specific siRNA injection into one-cell zygotes, of PHLDA2 and CDKN1C—which are located in the same gene cluster—resulted in significant changes in embryo development.

Accordingly, in one embodiment, the present invention provides a method of determining the likelihood of an embryo's developmental fate, the method comprising i) obtaining a supply of IVF embryos, and growing the embryos to a stage ready for planting into a uterus; ii) obtaining a single cell from the pre-planting embryos; iii) determining the expression level of at least a gene selected from the group consisting of CDKN1C, IGF2R, MAGEL2, MKRN3, NAP1L5, NDN, PEG3, PHLDA2, TSSC4, and UBE3A, and iv) planting into a uterus only embryos that do not show an increased expression level of the MKRN3, NDN, PEG3, PHLDA2, TSSC4, or UBE3A gene, or embryos that do not show a decreased expression level of the CDKN1C, IGF2R, MAGEL2, or NAP1L5 gene.

In one embodiment, the age of embryos from which cell can be extracted in the case of bovine is not more than 8 days.

In one embodiment, the gene expression level is determined by real time qRT-PCR on mRNA extracted from the single cell, preferably using an internal or a priori standard.

In another embodiment, the present invention provides a method of improving the likelihood of an embryo to develop successfully, the method comprising i) obtaining a supply of fertilized eggs, ii) micro-injecting siRNA of corresponding to the target gene into the fertilized eggs; and iii) continuing to cultivate the fertilized eggs until they are ready for planting into a uterus.

The embryos suitable for the above method of the present invention include those for the Florida panthers, giant pandas, black-footed ferrets, ocelots, clouded leopards, chimpanzees, gorillas, South American bush dogs, Mexican wolves, orangutans, and Mongolian wild horses.

DETAILED DESCRIPTION OF THE INVENTION

Figure 1:
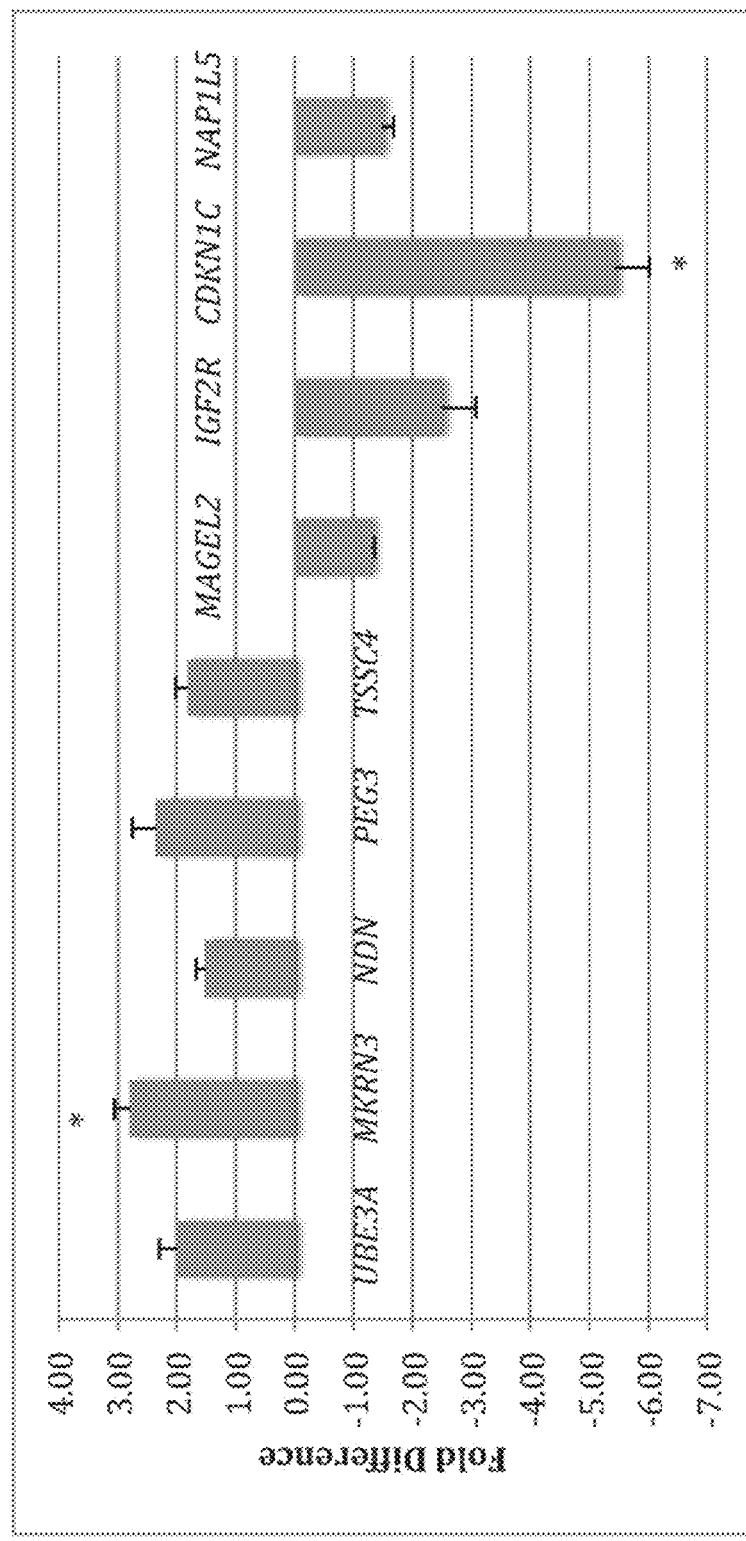
FIG. 1 shows the mean+S.E.M. for fold difference of degenerative relative to blastocyst embryo pools. Each bar represents the values across four sets of embryo pools (n=20 embryos per pool, two sires used). All samples were done in quadruplicates and normalized to GAPDH tested in the same cDNA samples. Expression calculations were done using the $2^{-\Delta\Delta Ct}$ method (59). Bars above the "0" represent genes that were up-regulated in degenerative embryos while bars below the "0" indicate down-regulated genes. * P<0.05.

The present invention in one embodiment provides a method of selecting an IVF embryo for planting in a uterus, the method comprising i) obtaining a supply of IVF embryos, and growing the embryos to a stage ready for planting into a uterus, ii) obtaining a cell from the pre-planting embryos; iii) determining the expression level of at least a gene selected from the group consisting of CDKN1C, IGF2R, MAGEL2, MKRN3, NAP1L5, NDN, PEG3, PHLDA2, TSSC4, and UBE3A, and iv) planting into a uterus only embryos that do not show an increased expression level of the MKRN3, NDN, PEG3, PHLDA2, TSSC4, or UBE3A gene, or embryos that do not show a decreased expression level of the CDKN1C, IGF2R, MAGEL2, or NAP1L5 gene.

In one embodiment, the embryo is at an age before hatching and is ready for planting. In one embodiment, the embryo is a bovine embryo. In another embodiment, the bovine embryo is not more than 8 days old, which has about 100-150 cells. In another embodiment, the embryo is at the morula stage or a stage where there is no differentiation; the morula stage bovine embryo consists of about 32 cells. The morula stage precedes the blastocyst stage. The blastocyst is a structure formed in the early development of vertebrates, and possesses an inner cell mass (ICM), or embryoblast, which subsequently forms the embryo, and an outer layer of cells, or trophoblast, which later forms the placenta. The trophoblast surrounds the inner cell mass and a fluid-filled blastocyst cavity known as the blastocoele or the blastocystic cavity. In humans the blastocyst consists of about 70-100 cells.

In one embodiment, the gene expression level is determined by real time qRT-PCR on mRNA extracted from the single cell, and using an internal standard, or a previously established standard. Methods of real time quantification of mRNA level are well-known to those ordinarily skilled in the art. See e.g. Galán A, Montaner D, Póo M E, Valbuena D, Ruiz V, Aguilar C, Dopazo J, Simón C. Functional genomics of 5- to 8-cell stage human embryos by blastomere single-cell cDNA analysis. PLoS One. 2010 Oct. 26; 5(10): e13615; Wang D., Bodovitz S. Single cell analysis: the new frontier in 'omics'. Trends in Biotechnology; 2010. p. 281-90, both of which are specifically incorporated herein by reference in their entirety.

Many methods of determining gene expression levels are known to persons ordinarily skilled in the art, e.g., as described in Sambrook et al. (eds.) Cloning: A Laboratory Manual, 2nd ed., Cold Spring Harbor Laboratory Press, 1989; Current Protocols in Molecular Biology (Ausubel et al. (eds.) New York: John Wiley and Sons, 1998). Examples of such methods include polymerase chain reaction (including absolute quantitation by PCR, real time PCR (RT-PCR) and qRT-PCR, multiplex or singleplex PCR), single cell PCR, northern blot assays, nuclease protection assays, in situ hybridization assays, immunohistochemistry assays, immunocytochemistry assays, electrophoresis assays such as gel or capillary, Western blot assays, ELISAs, immuno-precipitation assays, chromatography based assays such as HPLC or gel chromotography, mass spectrometry assays, RNase protection assays, flow cytometry assays, DNA methylation assays, and histone modification analysis assays.

In all methods of the invention, expression levels, at the RNA or at the protein level, can be determined using any suitable method. RNA levels may be determined by, e.g., quantitative RT-PCR (e.g., TaqMann™ RT-PCR), or as described in the Examples. Expression levels may be scaled and/or normalized per total amount of RNA or protein in the sample and/or a control, which may typically be a housekeeping gene such as the gene that encodes the beta-actin or glyceraldehyde-3-phosphate dehydrogenase (GAPDH), or 18S ribosomal RNA). Normalization is typically done using a standard curve to account for variability in the amount of protein, DNA, or RNA input, or environmental factors that affect the gene expression level.

In illustrative embodiments, the expression levels of the genes of interest are determined using RT-PCR, either by a standard curve for relative quantification. Absolute quantification of copy numbers may also be determined by preparing a standard curve using known amounts of the markers. The general methods for conducting such assays are described, e.g., in Real-Time PCR Systems: Applied Biosystems 7900HT Fast Real-Time PCR System and 7300/7500 Real-Time PCR Systems, Chemistry Guide, Applied Biosystems, 2005, Part No. 4348358 Rev. E.

The present invention in one embodiment provides a method of determining the likelihood of an embryo's developmental fate, the method comprising i) obtaining a supply of IVF embryos, and growing the embryos to a stage ready for planting into a uterus, ii) obtaining a single cell from the pre-planting embryos; and iii) determining the expression level of at least a gene selected from the group consisting of CDKN1C, IGF2R, MAGEL2, MKRN3, NAP1L5, NDN, PEG3, PHLDA2, TSSC4, and UBE3A, wherein embryos that do not show an increased expression level of the MKRN3, NDN, PEG3, PHLDA2, TSSC4, or UBE3A gene, or embryos that do not show a decreased expression level of the CDKN1C, IGF2R, MAGEL2, or NAP1L5 gene, are determined to be suitable for purposes of planting into a uterus for further development into successful pregnancy. Suitable embryos are then planted into uterus for further development.

In another embodiment, the present invention provides a method of improving the likelihood of an embryo to develop successfully, the method comprising i) obtaining a supply of fertilized eggs, ii) micro-injecting a suitable dosage of siRNA corresponding to the target gene into the fertilized eggs; and iii) continuing to cultivate the fertilized eggs until they are ready for planting into a uterus.

A small interfering RNA (siRNA) is a double-stranded RNA molecule capable of inhibiting or reducing the expression of a gene with which it shares homology. Each strand of the siRNA may be about 10 to about 50 nucleotides, about 12 to about 45 nucleotides, about 15 to about 40 nucleotides, about 20 to about 35 nucleotides, about 20 to about 30 nucleotides, or about 20 to about 25 nucleotides in length. The double stranded siRNA may have about 10 to about 50 base pairs, about 12 to about 45 base pairs, about 15 to about 40 base pairs, about 20 to about 35 base pairs, about 20 to about 30 base pairs, or about 20 to about 25 base pairs. One strand of the siRNA is called the target-complementary strand of an siRNA duplex. By "siRNA corresponding to a target gene," it is meant that the target-complementary strand of the siRNA is complementary to at least 10 nucleotides of the mRNA transcript of the target gene.

Alternatively, a single-stranded RNAi molecule may be assembled from a single oligonucleotide, where the self-complementary sense and antisense regions of the RNAi molecule are linked by means of a nucleic acid-based or non-nucleic acid-based linker(s). The RNAi molecule can be a polynucleotide with a duplex, asymmetric duplex, hairpin or asymmetric hairpin secondary structure. The RNAi can be a circular single-stranded polynucleotide having two or more loop structures and a stem comprising self-complementary sense and antisense regions. The circular polynucleotide can be processed either in vivo or in vitro to generate an active RNAi molecule.

Several methods have been used to deliver siRNAs to cells. These methods include delivering synthetic siRNA molecules into cells, such as the microinjection method described in the Examples, and vector-based methods in which siRNA is transcribed in a target cell by the vector. Certain vector-based siRNA delivery systems can result in persistent and effective suppression of gene expression. In many vector-based methods, the siRNA is generated by the production of small hairpin RNA or short hairpin RNA (shRNA). shRNA is a single-stranded RNA molecule comprising stem and hairpin structures. In such a system, an RNA polymerase III promoter, such as H1 promoter and U6 promoter, is used to drive transcription of shRNA. The shRNA is processed in the cell into siRNA through the action of the Dicer family of enzymes. Thus, the transcribed products mimic the synthetic siRNA duplexes and are effective for suppressing their corresponding target gene. U.S. Pat. No. 7,772,203; McIntyre G, Fanning G (2006), "Design and cloning strategies for constructing shRNA expression vectors," BMC Biotechnol. 6: 1; Paddison P, Caudy A, Bernstein E, Hannon G, Conklin D (2002). "Short hairpin RNAs (shRNAs) induce sequence-specific silencing in mammalian cells," Genes Dev. 16 (8): 948-58. shRNAs may be about 30 to about 80 (e.g., about 35, 40, 45, 50 or 55) nucleotides in length, specifically about 35 to about 70 nucleotides, about 35 to about 65 nucleotides, about 35 to about 60 nucleotides, about 35 to about 55 nucleotides, about 35 to about 50 nucleotides, or about 38 to about 44 (e.g., 38, 39, 40, 41, 42, 43 or 44) nucleotides in length. The double stranded region of the shRNA may have about 10 to about 35 base pairs, specifically about 12 to about 30 base pairs about 14 to about 25 base pairs, or about 16 to about 22 (e.g., about 16, 17, 18, 19, 20, 21 or 22) base pairs.

The embryos suitable for the above method of the present invention may be that of any animal, especially those for which artificial reproductive technologies are used due to low fertility, such as endangered animal species including the Florida panthers, giant pandas, black-footed ferrets, ocelots, clouded leopards, chimpanzees, gorillas, South American bush dogs, Mexican wolves, orangutans, and Mongolian wild horses.

The present invention further provides a method for selectively breeding cattle using a multiple ovulation and embryo transfer procedure (MOET), the method comprising superovulating a female animal, collecting eggs from said superovulated female, in vitro fertilizing said eggs and allow the fertilized eggs to develop into INF embryos, selecting for planting into a uterus only embryos that do not show an increased expression level of the MKRN3, NDN, PEGS, PHLDA2, TSSC4, or UBE3A gene, or embryos that do not show a decreased expression level of the CDKN1C, IGF2R, MAGEL2, or NAP1L5 gene. The selected embryo is then planted into a suitable uterus and allowed for further development.

The following examples are intended to illustrate preferred embodiments of the invention and should not be interpreted to limit the scope of the invention as defined in the claims.

Examples

Figure 5:
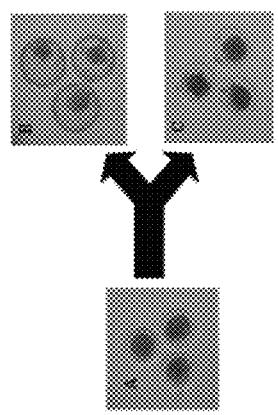
FIG. 5 shows the morphological assessment of embryos. Compacted morulas (A) that were cultured until day 8 of development and either showed signs of blastocoele formation (B) or degeneration (C).

Materials and Methods
In-Vitro Fertilization, Embryo Culture, and Morphological Grading
Ovaries from cows were obtained from a local abattoir and upon arrival underwent aspiration of antral follicles (2-6 mm). Maturation of oocytes and fertilization were accomplished by combining sperm, heparin, and PHE with the oocytes as described in Khatib et al. [2]. At day 5 of development all embryos underwent morphological assessment via light microscopy, where in vitro-produced embryos should reach approximately 16-32 cells and show evidence of cellular compaction and coalescence by this time. Embryos failing to show both of these properties were deemed "early degenerates" and removed from the study. Culturing and incubation was then continued until day 8 of development when the second morphological evaluation was performed. Embryos with a fluid filled cavity (blastocoele) giving evidence of cellular differentiation into the ICM and trophectoderm, were classified as "blastocysts" (FIG. 5). Embryos that showed compaction at day 5 but failed to form a blastocoele cavity were deemed as "late degenerates" (FIG. 5). These two populations of embryos were used for analysis and collected into RNALater (Ambion, Tex.) solution to preserve RNA integrity. For initial transcriptomic analysis, four randomly sampled pools of embryos (two blastocyst and two degenerate pools) were created (n=20 embryos/pool) using a single sire. A second set of pools (two blastocyst and two degenerate) was created (n=20 embryos/pool) using a second sire.

RNA Extraction and Amplification

Total RNA was extracted from the embryo pools using RNaqueous Micro (Ambion). Quality control of the RNA was performed using the RNA6000 NanoChip (Agilent Technologies, CA) with the Agilent 2100 Bioanalyzer to determine banding for 18S and 28S ribosomal RNA. Due to limitations in the amount of RNA in embryos, linear amplification was performed using the MessageAmp II aRNA amplification kit (Ambion). DNase I treatment was then performed using the RNaqueous Micro kit (Ambion) to ensure no genomic contamination in the samples.

Quantitative Real-Time RT-PCR (qRT-PCR).

The cDNA was synthesized from the amplified RNA using the iScript cDNA synthesis kit (Bio-Rad Laboratories, CA). Primers for qRT-PCR were designed using Beacon Software (Premier Biosoft, CA) to span exons if possible (Table 5). Six genes had only one exon (MAGEL2, MKRN3, NDN, H19, NAP1L5, and MIM1), and as such, DNase treatment of the RNA pools prior to cDNA synthesis was used to ensure no genomic contamination. In addition, PCR reactions were performed with DNase-treated RNA samples using primers designed in introns of the gene 7-dehydrocholesterol reductase (DHCR7) to test for the presence of genomic DNA in RNA samples. After two rounds of DNase treatment, no product was observed deeming the samples free of DNA contamination. An internal control gene for normalization was chosen using the Vandesompele method [58]. All imprinted genes underwent initial expression analysis to determine transcript abundance and those showing expression were then subsequently tested between morphological groups to quantify differential expression. The relative gene expression values were calculated using the $2^{-\Delta\Delta Ct}$ method [59]. Statistical analysis was performed using R version 2.15.2 (www.r-project.org/). The expression analysis for differentially expressed imprinted genes was analyzed using analysis of variance (ANOVA) of ΔCt values to determine possible sire and morphological effects.

Analysis of DNA Methylation of PHLDA2 by Bisulfite Sequencing

To evaluate the methylation status of PHLDA2, genomic DNA from embryo pools and tissues was treated with bisulfite and purified using the Epitect Bisulfite Kit (Qiagen). We performed the methylation analysis on pools of 20 blastocysts or degenerates. One pool for each of the developmental statuses was evaluated. Nonetheless, embryos were collected at multiple times to obtain the sufficient number of embryos in the pools. Bisulfite-treated DNA was first amplified by a PCR reaction for 40 cycles. The PCR products were gel purified and amplified in a second PCR reaction for 18 cycles using the same primers. The PCR products were gel purified, ligated to the pGEM-T Vector (Promega, WI), and transformed into JM101 competent cells (Promega) following the manufacturer's instructions. Bacterial colonies were screened for the presence of a single copy of insert fragment by PCR with primers pairing with vector sequences flanking the TA cloning site. Each embryo on average contained 100-150 cells. Thus there were a total of approximately 4000-6000 chromosomes in the pool. We sequenced ~20 clones and selected only those with the highest quality of sequence before looked at their actual sequences. The PCR products were sequenced to obtain bisulfite-converted DNA sequences. Association between DNA methylation at each CpG site with developmental status or tissue was tested by Fisher's exact test. Only CpG sites with a combined (two samples in comparison) methylation level between 10% and 90% were tested, and statistical significance was declared at a $P<0.01$.

siRNA Design and Synthesis siRNA sequences were designed and synthesized by Sigma-Aldrich (St. Louis, Mo.). A BLAST of siRNA sequences was done against the bovine mRNA reference sequence to ensure that there would be minimal off-target effects. Research has shown that naturally produced siRNA have a 5'-phosphate on the antisense strand that participates in activation of the RNA induced silencing complex (RISC) [60]. Although most synthetically-produced siRNAs have a 5'-OH (antisense), ATP-dependent phosphorylation occurs shortly after introduction into the cell [60]. Given that we are injecting siRNA into a newly developing embryo with limited stores of ATP, a 5'-Phosphorylation modification was added to minimize reduction of energy stores in the embryo. The siRNA duplex sequences were PHLDA2 antisense [Phos]AGUAGCACCGGGCUAUAUCdTdT (SEQ ID No. 1), PHLDA2 Sense GAUAUAGCCCGGUGCUACUdTdT (SEQ ID No. 2), CDKNJC antisense [Phos]AAAUCC-CUGAGUGCGGCGGdTdT (SEQ ID No. 3), and CDKNJC sense CCGCCGCACUCAGGGAUUUdTdT (SEQ ID No. 4). For siRNA injection three concentrations were assessed (100 uM, 150 uM, 200 uM).

Experimental Controls

Two control groups were designed to help infer effects of single-gene knockdown. In the first control group (sham control), embryos underwent mechanical puncturing by the microinjection needle but no siRNA delivery in order to assure that potential phenotypic observations are due to the siRNA, and not a result of mechanical damage due to injection. The second group was a baseline control that consisted of embryos produced by our conventional IVF system.

Embryo Preparation and Microinjection of siRNA

In vitro maturation followed the protocol outlined in Khatib et al. [2] except that putative zygotes were incubated for 18-hours. After this period, zygotes were removed from fertilization media, denuded of cumulus-complexes, and then prepared for microinjection. Microinjection of the zygotes was performed using an inverted Nikon Diaphot microscope (200× magnification) as described by Nganvongpanit et al. [15] with some modifications. In summary, a group of 25-35 zygotes were placed in a droplet of TALP-Hepes wash media with a mineral oil overlay. A microinjection needle was used to pierce the zona pellucida and deposit approximately ~7-10 picoliters of siRNA into the cytoplasm of the zygote using the MINJ-D pressurized microinjection system (Tritech Research, CA). Zygotes were then washed twice in TALP-HEPES wash media post-injection and placed in SOF culture medium and incubated under the parameters mentioned above.

Morphological Grading

Cleavage rates were assessed as a marker of fertilization for this study. In addition, embryos were assessed on day 8 of culture for blastocyst development. Embryos at the blastocyst stage were collected from each treatment group and underwent RNA extraction, cDNA synthesis, and qRT-PCR as outlined in the previous sections. Comparison of cleavage and blastocyst rates was completed using a chi-squared test for contingency with statistical significance deemed at $P<0.05$.

RNA-Seq Pathway Analysis of siRNA and Non-siRNA Injected Embryos

Total RNA from control, sham-injected, and siRNA-injected CDKN1C embryo pools underwent amplification using the MessageAmp II aRNA Amplification Kit (Ambion). Libraries of amplified RNA for each pool were prepared following the Illumina mRNA-Seq protocol. Sequencing libraries were created from 50 ng samples and sequenced with Illumina's HiSeq 2000 at the University of Wisconsin-Madison Biotechnology Center. Mapping reads to the bovine reference genome, assembly of transcripts and estimation of differential expression, and Gene Ontology (GO) enrichment analysis was performed as described in Driver et al. [61]. Sequencing reads were mapped to the reference genome (bosTau7) using the software package Tophat (v2.0.4) [62]. Cufflinks (v2.0.2) was used to assemble transcript models from alignments and to estimate their abundance in the transcriptome [63]. Abundances of transcripts were upper-quartile normalized and also corrected for sequence bias in order to improve expression estimates [64]. Differential expression of genes was tested using Cuffdiff, a tool part of the Cufflinks package for testing differential gene expression [63]. In addition, GO enrichment analysis was performed using the GOseq (v1.8.0) package [65] that is available in the R language/environment. Biological pathways with a FDR<0.10 were considered significant.

Results

Association of Expression Levels of Imprinted Genes with Pre-Implantation Bovine Embryo Development In a previous study, we used microarrays to profile gene expression of IVF embryos showing distinct developmental statuses. Among the differentially expressed genes, PHLDA2 was found to be significantly up-regulated in degenerate embryos as compared to normally developed blastocysts in both microarray and qRT-PCR experiments [3]. Given that PHLDA2 is imprinted and that imprinted genes have key roles in embryo development, we sought to assess whether other imprinted genes may show association with developmental status of the embryo. Nine genes (CDKN1C, IGF2R, MAGEL2, MKRN3, NAP1L5, NDN, PEG3, TSSC4, and UBE3A) were detected in pools of blastocyst and degenerate embryo populations with quantifiable differential expression. NDN, TSSC4, UBE3A, PEG3, and MKRN3 were found to be up-regulated in degenerate embryos showing average 1.5±0.17-fold, 2.0±0.22-fold, 2.0±0.31-fold, 2.4±0.30-fold, and 2.8±0.26-fold differences between pools, respectively (FIG. 1). The genes MAGEL2, NAP1L5, IGF2R, and CDKN1C showed average 1.3±0.04-fold, 1.5±0.2-fold, 2.5±0.57, and 5.4±0.58-fold up-regulation in blastocysts, respectively (FIG. 1). Of those differentially expressed, MKRN3 ($P=0.031$) and CDKN1C ($P=0.035$) showed statistically significant differences in expression between blastocyst and degenerate embryos, and PEG3 had differential expression that was close to a level of significance ($P=0.057$). Four genes (USP29, NNAT, PEG10, and RTL1) had very low expression in embryos making it impossible to quantify differences accurately, while three genes (IGF2, H19, and MIM1) had undetectable levels of expression in our embryo populations. To reveal the mechanisms underlying the differential expression observed in pre-implantation embryos, PHLDA2 and CDKN1C were selected for further functional analysis.

Figure 2:
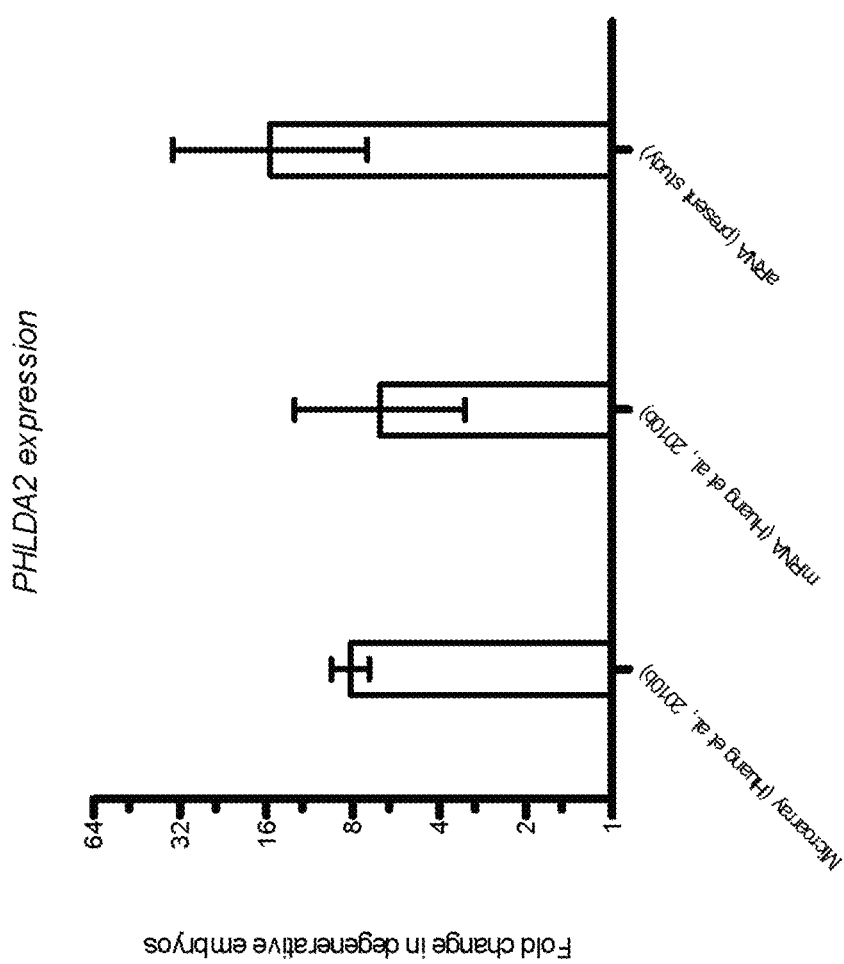
FIG. 2 shows the differential expression of PHLDA2 in IVF blastocysts and degenerate embryos. Data for PHLDA2 expression from microarrays and mRNA was obtained from Huang et al. [5], incorporated herein by reference in its entirety. Expression of PHLDA2 was normalized to GAPDH and shown as fold change (±SD) in degenerate embryos.

DNA Methylation of PHLDA2 is Associated with Differential Expression and Tissue Specificity In this study, the up-regulation of PHLDA2 was reconfirmed in three additional pairs of biological replicates, showing 15-fold higher expression in degenerates compared to blastocysts (FIG. 2). Although the magnitudes of difference varied between pairs of embryos and between studies, PHLDA2 expression was consistently higher in degenerate embryos than in blastocysts. These results clearly suggest an association between aberrant PHLDA2 expression and abnormal early embryonic development in IVF embryos.

TABLE 1

Development rates for PHILDA2 siRNA-injected and control embryo groups

| Treatment | Total | Cleaved | Cleavage Rate | Blastocysts | Blastocyst Rate |
| --- | --- | --- | --- | --- | --- |
| Control | 279 | 208 | 74%$^a$ | 54 | 26%$^a$ |
| Sham | 249 | 191 | 77%$^a$ | 49 | 26%$^a$ |
| 100 uM | 138 | 89 | 64%$^a$ | 33 | 37%$^a$ |
| 150 uM | 65 | 45 | 69%$^a$ | 11 | 24%$^a$ |
| 200 uM | 145 | 98 | 68%$^a$ | 10 | 10%$^b$ |

Differing superscripts within a column denote statistically significance difference at $P < 0.05$.

Figure 3:
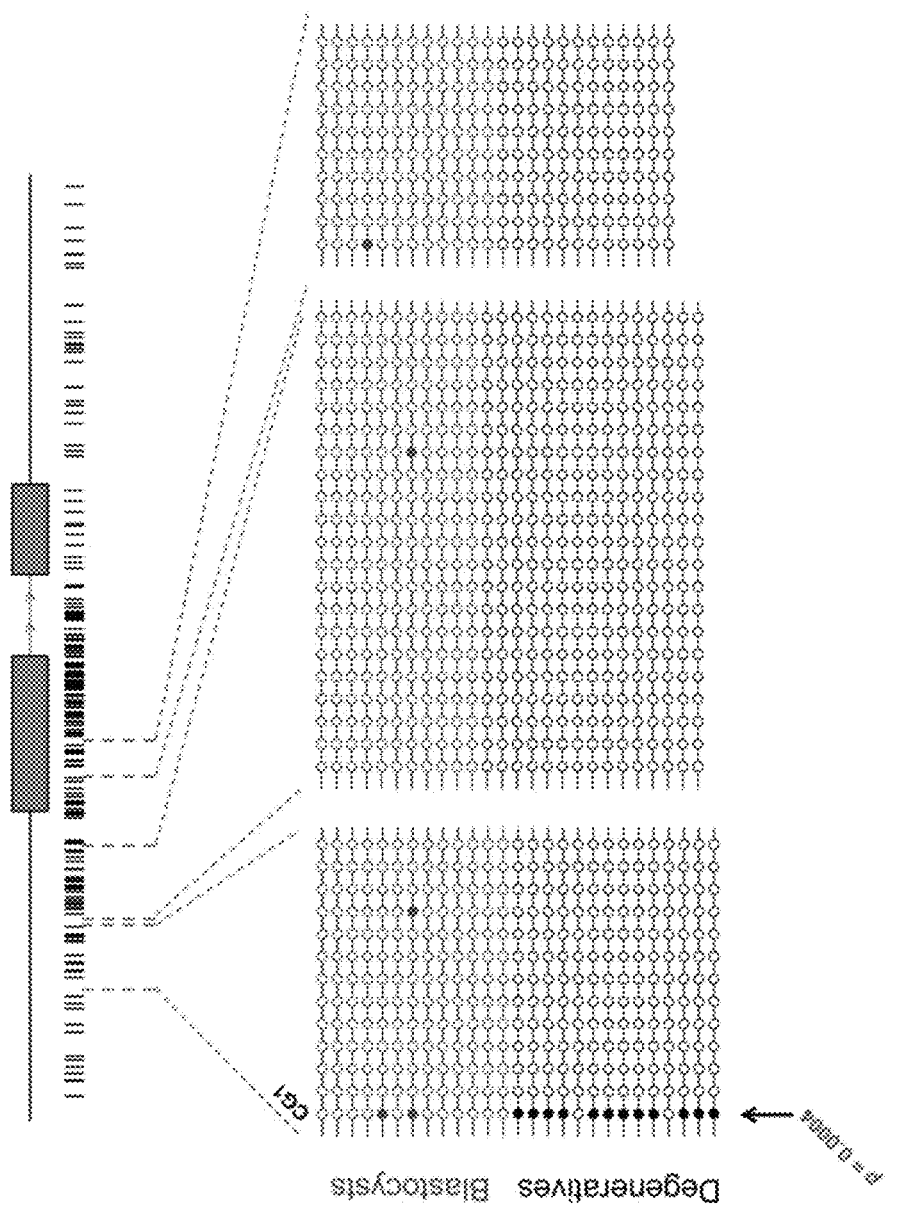
FIG. 3 shows the DNA methylation of PHLDA2 in IVF embryos. Exons of PHLDA2 are indicated by grey boxes and the direction of transcription is indicated by arrowheads. Vertical bars below the gene model represent CpG sites near and within PHLDA2. The CpG island overlapping with PHLDA2 is shown as an open rectangular box. For methylation analysis, each row of circles connected by a line represents a single clone. Filled circles indicate methylated CpGs while open circles represent unmethylated CpGs. Clones derived from blastocysts and degenerate embryos are shown in red and black respectively. CpG sites tested for differential methylation are marked by arrows. Significant differential methylation of CpG sites are indicated by p values.
Figure 6:
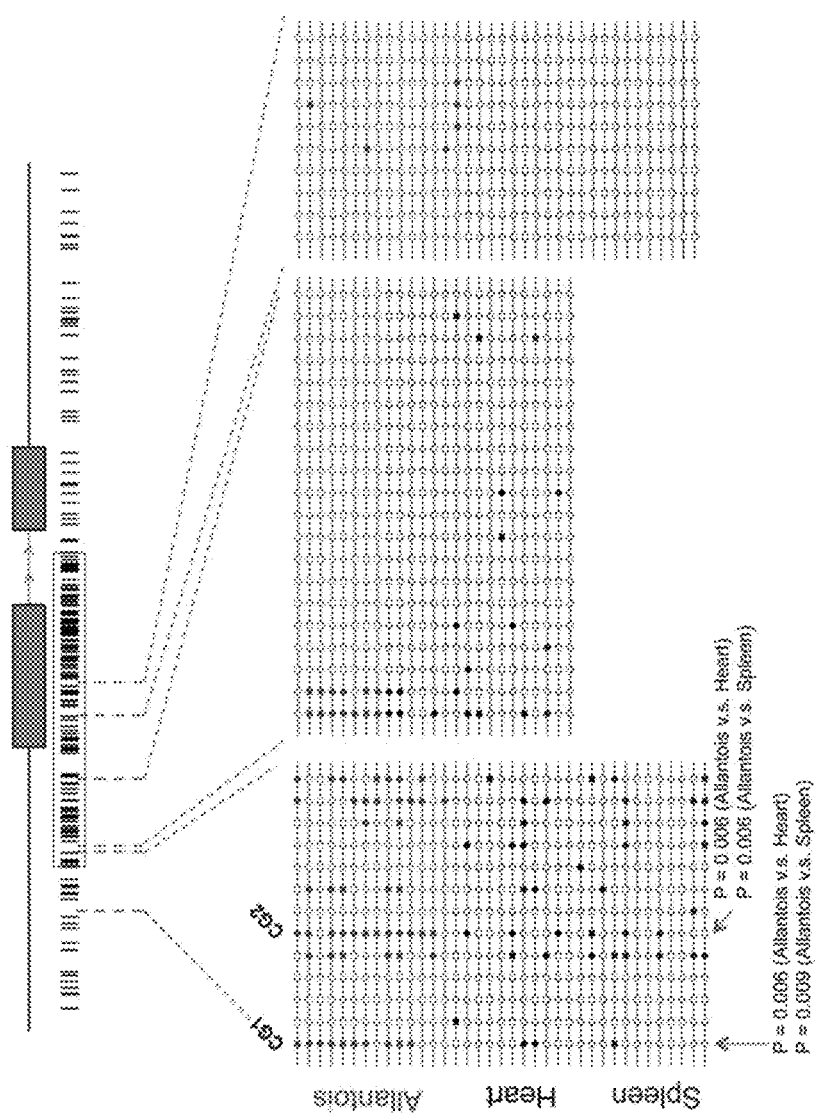
FIG. 6 shows DNA methylation of PHLDA2 in bovine tissues. Clones from allantois, heart, and spleen DNA are shown in red, black, and blue, respectively.

Because of the importance of DNA methylation in regulating transcription—particularly that of imprinted genes—we measured the methylation of cytosines at CpG sites near or within the PHLDA2 gene by bisulfate sequencing. A CpG island highly enriched for CpG sites was found to overlap with the first exon and first intron of PHLDA2 as well as upstream of the start of the transcript. DNA methylation analysis of blastocysts and degenerate embryos revealed rare methylation of CpG cytosines (FIG. 3). However, one CpG site upstream of the PHLDA2 transcription start site was highly methylated in degenerate embryos relative to blastocysts (FIG. 3, $P=0.0004$). To test whether DNA methylation was associated with the tissue specificity of PHLDA2 expression and imprinting, we measured methylation of DNA from heart, where PHLDA2 was not expressed; from spleen, where PHLDA2 was lowly expressed and not imprinted; and from allantois, where PHLDA2 was highly expressed and imprinted (FIG. 6). Interestingly, DNA upstream of PHLDA2 was methylated at a higher level in allantois than in heart and spleen (FIG. 6). In particular, the same CpG dinucleotide (CG1 in FIG. 3) that was associated with PHLDA2 expression in embryos was methylated at a higher level in allantois than in heart and spleen (FIG. 6). A similar methylation pattern was also observed for another CpG site nearby (CG2; FIG. 6).

PHLDA2 has Dosage-Sensitive Effects on Bovine Pre-Implantation Embryo

To test whether artificially suppressing expression of PHLDA2 changes embryonic development, we injected fertilized zygotes with siRNA oligos targeting PHLDA2 mRNA. Microinjection of 200 uM siRNA specific to PHLDA2 resulted in a 10% development rate versus 26% for the control group (P=0.0004), whereas microinjection of 150 uM siRNA resulted a development rate similar to the control group (Table 1). In contrast, microinjection of 100 uM siRNA caused an increase in blastocyst development (37%) relative to the control group (26%) (Table 1). To test the effect of the 100 uM siRNA injection on embryo development under different environmental conditions, oocytes were collected from ovaries in mid-summer during a period of heat stress where bovine embryo development shows a marked decrease. After fertilization, microinjection and subsequent culturing were performed. During the heat stress period, the development rate of blastocysts in the control group was 5% compared to 15% in the 100 uM-injected group (P=0.02) (Table 6). In addition, there was a significant difference in cleavage rate for the 150 uM group (P=0.047) compared to the control group. In a subsequent microinjection experiment done at the end of the heat stress season, the development rate of blastocysts was 25% in the 100 uM injected group compared to 20% and 18.35% in the control and sham groups, respectively (Table 7).

Figure 4:
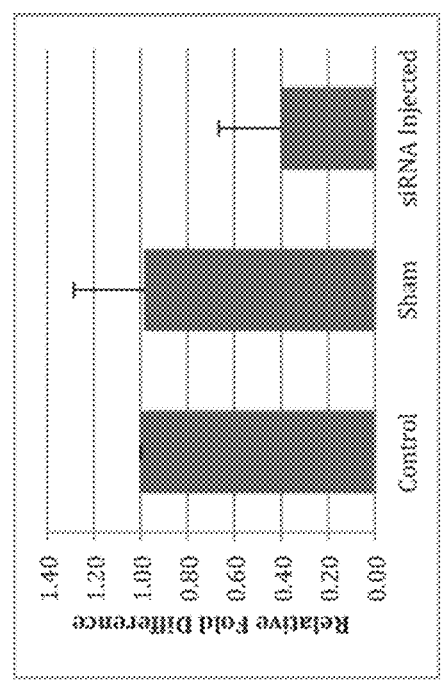
FIG. 4 shows the qRT-PCR results for control and CDKN1C siRNA injections. All samples were normalized to GAPDH using the ΔΔCt method [59].
Figure 7:
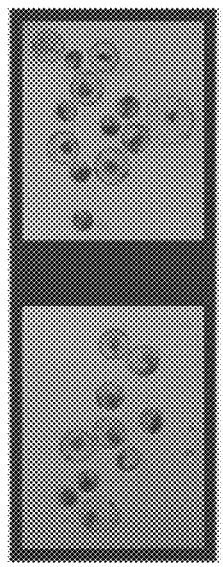
FIG. 7 shows the morphological comparison of blastocysts on day 8 of culture. Box A (left) shows a representative sample of blastocysts that were injected with CDKN1C siRNA. Box B (right) shows representative samples of control (non-injected) blastocysts.

Knockdown of CDKN1C Using siRNA Affects Bovine Pre-Implantation Embryonic Development We also tested the effect of CDKN1C knockdown on pre-implantation embryonic development. Initial siRNA experiments with different concentrations showed that 200 uM of siRNA produced ≥50% knockdown of CDKN1C gene expression in blastocysts collected on day 8 of culture. As such, this concentration was selected for further microinjection analysis. Injection of 200 uM CDKN1C siRNA resulted in 45% decrease in blastocyst rate (P<0.0006) by day 8 of development (Table 2). To determine the amount of knockdown achieved by siRNA injection, qRT-PCR was performed in the baseline control and the injected embryos. FIG. 4 shows 50% knockdown in gene expression. There was no significant difference in cleavage rate and blastocyst rate for the sham, siRNA injected, and control group in any of the IVF replications (P=0.973). Furthermore, phenotypic observations showed no marked difference between blastocysts produced from the baseline control or from CDKN1C injections (FIG. 7).

TABLE 2

Development rates for CDKN1C siRNA-injected embryos and control embryo groups

| Treatment | Total$^a$ | Cleaved | Cleavage Rate | Blastocysts | Blastocyst Rate |
|---|---|---|---|---|---|
| Control | 372 | 288 | 77%$^a$ | 70 | 24%$^a$ |
| Sham | 327 | 251 | 77%$^a$ | 59 | 24%$^a$ |
| CDKN1C siRNA 200 uM | 354 | 272 | 77%$^a$ | 34 | 13%$^b$ |

$^a$Numbers represent average of six biological replicates;
Differing superscripts within a column denotes statistically significant differences (P < 0.05)

TABLE 3

Genes differentially expressed between sham and injected embryos using RNA-Seq.

| Gene | Locus (bosTau7) | log2 (fold_change) | fold_change | Overexpression | qvalue | qvalue |
|---|---|---|---|---|---|---|
| IFI6 | chr2: 131115858-131119447 | −6.32041 | 79.92 | I | 2.04E−07 | 0.000 |
| IFI27 | chr21: 59014080-59022973 | −6.16491 | 71.75 | I | 0.0285423 | 0.029 |
| BID | chr5: 115412156-115418905 | 5.43679 | 43.31 | S | 0.00611461 | 0.006 |
| CCDC80 | chr1: 58080017-58115541 | −5.26498 | 38.45 | I | 0.00536579 | 0.005 |
| ISG15 | chr16: 48676752-48677780 | −5.20855 | 36.98 | I | 0.0123406 | 0.012 |
| LUM | chr5: 23650318-23657534 | −5.10874 | 34.51 | I | 6.68E−05 | 0.000 |
| PHACTR3 | chr13: 57213274-57279363 | −5.00485 | 32.11 | I | 0.104192 | 0.104 |
| LOC100335809 | chr2: 6670518-6681740 | −4.95429 | 31.00 | I | 7.00E−05 | 0.000 |
| GJA1 | chr9: 31507202-31520216 | −4.88782 | 29.61 | I | 0.000315737 | 0.000 |
| XCL1 | chr16: 33520304-33523470 | −4.82608 | 28.37 | I | 0.00112997 | 0.001 |
| C27H8orf4 | chr27: 37380049-37381351 | −4.55854 | 23.56 | I | 0.000833725 | 0.001 |
| AMY2B | chr3: 42379420-42402070 | −4.54654 | 23.37 | I | 0.0519033 | 0.052 |
| LOC510631 | chr7: 41563878-41567475 | −4.40798 | 21.23 | I | 6.68E−05 | 0.000 |
| RARRES2 | chr4: 116419569-116422625 | −4.3782 | 20.80 | I | 0.000833725 | 0.001 |
| PLOD2 | chr1: 124617975-124739559 | −3.91289 | 15.06 | I | 0.000151231 | 0.000 |
| OLR1 | chr5: 106703848-106715154 | −3.7881 | 13.81 | I | 0.0667877 | 0.067 |
| CSRP3 | chr29: 26759118-26779797 | −3.69731 | 12.97 | I | 0.104192 | 0.104 |
| VIM | chr13: 31432087-31440017 | −3.66348 | 12.67 | I | 0.00611461 | 0.006 |
| CDH2 | chr24: 29398109-29646615 | −3.55893 | 11.79 | I | 0.00611461 | 0.006 |
| BMP2 | chr13: 49207397-49218698 | −3.36487 | 10.30 | I | 0.0857017 | 0.086 |
| GATM | chr10: 66442207-66458222 | −3.25909 | 9.57 | I | 0.0015428 | 0.002 |
| TST | chr5: 80585175-80591756 | 3.19801 | 9.18 | S | 0.172886 | 0.173 |
| RNASEH2A | chr7: 10989463-10996393 | 3.17779 | 9.05 | S | 0.104192 | 0.104 |
| LOC515823 | chr10: 75128125-75129562 | 3.1723 | 9.01 | S | 0.11784 | 0.118 |
| ETHE1 | chr18: 51364563-51383878 | 3.12143 | 8.70 | S | 0.0133299 | 0.013 |
| LOC100850219 | chr5: 25327382-25336652 | −2.94068 | 7.68 | I | 0.0159411 | 0.016 |
| LOC788610 | chr15: 47867002-47868681 | 2.90533 | 7.49 | S | 0.0667877 | 0.067 |
| HBG | chr15: 47852891-47854506 | 2.88532 | 7.39 | S | 0.0527532 | 0.053 |
| — | chrUn_AAFC03100583: 48768-54903 | 2.85006 | 7.21 | S | 0.194133 | 0.194 |
| LOC100849362 | chrY: 3503924-3652372 | 2.83774 | 7.15 | S | 0.0298012 | 0.030 |
| SLC7A4 | chr17: 75507216-75510133 | 2.81633 | 7.04 | S | 0.129536 | 0.130 |
| UCHL1 | chr6: 62454747-62466453 | −2.79919 | 6.96 | I | 0.162185 | 0.162 |
| SLITRK2 | chrX: 17410200-17413598 | −2.74863 | 6.72 | I | 0.15962 | 0.160 |
| LOC507211 | chr9: 31659066-31826452 | 2.71243 | 6.55 | S | 0.11784 | 0.118 |
| GLCCI1 | chr4: 16107848-16217411 | −2.70933 | 6.54 | I | 0.194133 | 0.194 |
| BIRC3 | chr15: 5391794-5422552 | −2.70615 | 6.53 | I | 0.0667877 | 0.067 |

TABLE 3-continued

Genes differentially expressed between sham and injected embryos using RNA-Seq.

| Gene | Locus (bosTau7) | log2 (fold_change) | fold_change | Overexpression | qvalue | qvalue |
|---|---|---|---|---|---|---|
| PLSCR1 | chr1: 124197036-124224862 | -2.67092 | 6.37 | I | 0.0519033 | 0.052 |
| FAM110A | chr13: 60912609-60926339 | 2.66448 | 6.34 | S | 0.129536 | 0.130 |
| WBP1 | chr11: 10572506-10574898 | 2.656 | 6.30 | S | 0.104192 | 0.104 |
| KIF7 | chr21: 20902079-20919879 | -2.54852 | 5.85 | I | 0.0386798 | 0.039 |
| SRM | chr16: 39298009-39302069 | 2.40596 | 5.30 | S | 0.0800995 | 0.080 |
| XIST | chrX: 47265732-47302267 | -2.34036 | 5.06 | I | 0.0671875 | 0.067 |
| CIB1 | chr21: 21450599-21453772 | 2.32354 | 5.01 | S | 0.0826982 | 0.083 |
| TPRG1L | chr16: 46723485-46726372 | 2.30358 | 4.94 | S | 0.118303 | 0.118 |
| RNASE1 | chr10: 25672191-25673775 | 2.29757 | 4.92 | S | 0.171802 | 0.172 |
| CCNL1 | chr1: 111988773-112002656 | -2.2819 | 4.86 | I | 0.11784 | 0.118 |
| NID2 | chr10: 44859533-44958463 | -2.23342 | 4.70 | I | 0.121965 | 0.122 |
| AP2S1 | chr18: 53642812-53652534 | 2.23307 | 4.70 | S | 0.171802 | 0.172 |
| OGT | chrX: 48728453-48754810 | -2.13832 | 4.40 | I | 0.195152 | 0.195 |
| FAT1 | chr27: 17621364-17747563 | -2.1212 | 4.35 | I | 0.15962 | 0.160 |
| IFNT2 | chr8: 23602560-23603873 | -2.11584 | 4.33 | I | 0.15962 | 0.160 |

S—SHAM
I—INJECTED

Transcriptomic Response of Embryos Upon CDKN1C Knockdown

To better understand the mechanisms by which CDKN1C affects embryo survival, we analyzed the global RNA expression patterns in control, sham, and injected embryos using RNA-Seq. Comparative analysis of individual genes between sham- and siRNA-injected embryos revealed 51 genes that were differentially expressed between the two embryo groups (Table 3). GO analysis uncovered nine pathways significantly enriched for differentially expressed genes (FDR<0.10) between sham-injected and CDKN1C siRNA-injected embryos (Table 4). Of these, there appears to be a preponderance of perturbation to cellular signaling/communication (extracellular region, regulation of cell communication), nucleic acid processing (endonuclease activity, endoribonuclease activity, producing 3'-phosphomonoesters), and cellular metabolism (monosaccharide catabolic process, alcohol catabolic process, and various carbohydrate catabolic processes).

TABLE 4

Pathways significantly enriched for differentially expressed genes

| GO ID | Ontology | Term |
|---|---|---|
| 0005576 | CC | Extracellular region |
| 0016894 | MF | Endonuclease activity, active with either ribo- or deoxyribonucleic acids and producing 3'-phosphomonoesters |
| 0046365 | BP | Monosaccharide catabolic process |
| 0044421 | CC | Extracellular region part |
| 0010646 | BP | Regulation of cell communication |
| 0046164 | BP | Alcohol catabolic process |
| 0044275 | BP | Cellular carbohydrate catabolic process |
| 0016892 | MF | endoribonuclease activity, producing 3'-phosphomonoesters |
| 0016052 | BP | Carbohydrate catabolic process |

Notes:
Pathways significantly enriched (FDR < 0.10) for differentially expressed genes between sham and CDKN1C siRNA-injected embryos. Pathways are ranked in order of decreasing statistical significance
BP: Biological process;
CC: Cellular component;
MF: Molecular function

TABLE 5

Primer sequences for real-time PCR reactions and product sizes

| Gene | Primer | Sequence (5'-3') | Amplicon (bp) |
|---|---|---|---|
| UBE3A | Forward | GGGACTCTGTTGTGATTAGGG (SEQ ID No. 5) | 171 |
|  | Reverse | TAGGTAACCTTTCTGTGTCTGG (SEQ ID No. 6) |  |
| NDN[a] | Forward | AACGTGCTGCGCATCTTG (SEQ ID No. 7) | 103 |
|  | Reverse | TCAGGTAGTTCTGCTGGACGAA (SEQ ID No. 8) |  |
| MAGEL2[b] | Forward | CTGATGGTGGTTCTGAGCCT (SEQ ID No. 9) | 257 |
|  | Reverse | CAGGACAATCATCTTGCTGG (SEQ ID No. 10) |  |
| MKRN3 | Forward | CTGCAGACAGCGGCCCTAGC (SEQ ID No. 11) | 222 |
|  | Reverse | CCCGGTAGGGTTGCCCAGGA (SEQ ID No. 12) |  |
| CDKN1C | Forward | CAAGCGGCTGCGATGAGAG (SEQ ID No. 13) | 67 |
|  | Reverse | TCCTGTCCACTGCCCAACG (SEQ ID No. 14) |  |
| IGF2R | Forward | CAGTCGCAAAGTCGGAACC (SEQ ID No. 15) | 140 |
|  | Reverse | GGTCACAGTGGAAGAAGATGG (SEQ ID No. 16) |  |
| PEG.3[c] | Forward | CGCCAAAGTCAGGGAGAG (SEQ ID No. 17) | 150 |
|  | Reverse | CTTAACTGCCAGGACACC (SEQ ID No. 18) |  |

TABLE 5-continued

Primer sequences for real-time PCR reactions and product sizes

| Gene | Primer | Sequence (5'-3') | Amplicon (bp) |
|---|---|---|---|
| NAP1L5 | Forward | TCCTTTCGTCACAGTATCGC (SEQ ID No. 19) | 118 |
| | Reverse | TGAGTTCTGCTGCTGCTG (SEQ ID No. 20) | |
| TSSC4 | Forward | TGCCACCAAGAACCTTCG (SEQ ID No. 21) | 106 |
| | Reverse | CCTCTGCCATGTGTCACC (SEQ ID No. 22) | |
| PEG10 | Forward | CTTTCCAGCCTTCGCAGAG (SEQ ID No. 23) | 126 |
| | Reverse | CTTCACTCCTGTGGCAATGG (SEQ ID No. 24) | |
| USP29 | Forward | AGGAGGAAGTTCCCTTTGTTGC (SEQ ID No. 25) | 143 |
| | Reverse | TCTCTGTGACGGCTGAAATAGC (SEQ ID No. 26) | |
| RTL1 | Forward | CCCTCCTCTACCACCCCAAG (SEQ ID No. 27) | 107 |
| | Reverse | CTTGCCCGTCCGCTTGTC (SEQ ID No. 28) | |
| NNAT | Forward | CACCCACCCACCAGTCTC (SEQ ID No. 29) | 142 |
| | Reverse | TTCTCGACACCGTGTATGC (SEQ ID No. 30) | |
| MIM1 | Forward | ACTCGGTTGTCAGTCACAC (SEQ ID No. 31) | 115 |
| | Reverse | GAATTTCCATCGTCTTATTAGC (SEQ ID No. 32) | |
| IGF2 | Forward | TGCTGCTATGCTGCTTACC (SEQ ID No. 33) | 151 |
| | Reverse | AACACTCTTCCACGATGCC (SEQ ID No. 34) | |
| H19 | Forward | CGTTCCTTTAGTCTCCTGAC (SEQ ID No. 35) | 119 |
| | Reverse | AGTCCGTGTTCCAAGTCC (SEQ ID No. 36) | |
| XIST | Forward | CCACTGAGCAACAACTCTAGG (SEQ ID No. 37) | 126 |
| | Reverse | GGCAAATATGAAGGGAACAACC (SEQ ID No. 38) | |
| P.O. | Forward | GACAATGGCAGCATCTAC (SEQ ID No. 39) | 198 |
| | Reverse | GAAGGTGTAATCAGTCTCC (SEQ ID No. 40) | |
| B-ACTIN | Forward | AGGCCAACCGTGAGAAGATGAC (SEQ ID No. 41) | 100 |
| | Reverse | CCAGAGGCATACAGGGACAGC (SEQ ID No. 42) | |
| GAPDH | Forward | TGCCCAGAATATCATCCC (SEQ ID No. 43) | 134 |
| | Reverse | AGGTCAGATCCACAACAG (SEQ ID No. 44) | |

[a]NDN primers referenced from Wee et al. [66]
[b]MAGEL2 primers referenced from Tveden-Nyborg et al. [29]
[c]PEG3 primers referenced from Katz-Jaffee et al. (2008)

TABLE 6

Injection of 100 uM and 150 uM PHLDA2 siRNA under heat stress

| Treatment Group | Total | Cleaved | Cleavage Rate | Blastocysts | Blastocyst Rate |
|---|---|---|---|---|---|
| Control | 166 | 123 | 68%[a] | 6 | 5%[a] |
| PHLDA2 siRNA 100 uM | 70 | 48 | 68%[a] | 8 | 15%[b] |
| PHLDA2 siRNA 150 uM | 74 | 43 | 61%[b] | 2 | 4%[a] |

Differing superscripts within a column denote statistically significant differences (P < 0.05).

TABLE 7

Injection of 100 uM and 150 uM PHLDA2 siRNA under presumptive post-heat stress

| Treatment Group | Total | Cleaved | Cleavage Rate | Blastocysts | Blastocyst Rate |
|---|---|---|---|---|---|
| Control | 105 | 70 | 66.7% | 14 | 20% |
| Sham | 96 | 54 | 56.25% | 10 | 18.25% |
| PHLDA2 siRNA 100 uM | 97 | 64 | 65.98%* | 16 | 25% |
| PHLDA2 siRNA 150 uM | 125 | 91 | 72.8% | 17 | 18.68% |

*denotes P < 0.05

Discussion

Association of DNA Methylation with Expression of PHLDA2

The regulatory mechanisms of PHLDA2 expression and its imprinting are not well understood in cattle. DNA methylation is one of the most common mechanisms in regulating transcription. In mammals, a general rule is that methylation in promoter regions of genes represses transcription initiation whereas methylation in gene bodies enhances transcription elongation [20]. In bovine IVF embryos at the blastocyst stage, CpG sites within or near the PHLDA2 gene were generally not methylated (FIG. 3). Nevertheless, the methylation of a CpG site upstream of PHLDA2 was associated with higher expression of the gene in degenerate embryos. This particular CpG site was near the boundary of the CpG island overlapping with PHLDA2. In fetal tissue DNA, PHLDA2 was methylated at a higher level in heart, spleen, and allantois than in embryos, particularly in the region outside the CpG island. Interestingly, the same CpG site whose methylation correlated with expression in embryos also showed differential methylation between heart, spleen, and allantois DNA (FIG. 6). While this CpG site was highly methylated in allantois, its methylation was lower in heart and spleen. PHLDA2 expression in allantois was extremely high while it was relatively lower in spleen and not detected in heart. The differential methylation of the two CpG sites in these three tissues suggests correspondence with PHLDA2 expression.

Recent studies have clearly established that while a negative correlation exists between DNA methylation in promoter regions and gene expression, intragenic methylation is abundant and that this methylation is positively correlated with gene expression [21-23]. Thus, the increase in gene expression observed when CG1 in degenerate embryos and CG1 and CG2 in allantois were methylated is consistent with these studies.

Dosage Sensitivity of PHLDA2 in Bovine Pre-Implantation Embryos

Injections of 100 uM siRNA increased development from 26 to 37%, while more concentrated knockdown using 200 uM siRNA caused significant decrease in blastocyst rate (control 27% vs. 10%). This dosage-sensitive effect of PHLDA2 was not only evident in our standard IVF system, but also in the presence of relatively adverse developmental conditions. Heat stress is a known condition that negatively affects the reproductive function in dairy cattle, which in turn leads to a decrease in embryonic development [24-27]. Production of IVF embryos during heat stress and in the end of heat stress season resulted in low blastocyst rates in the control group of non-injected embryos (Table 6 and Table 7). In contrast, embryos that were injected with 100 uM PHLDA2 siRNA had an increased blastocyst rate relative to controls. Thus, regardless of environmental conditions, internal roles of PHLDA2 can improve or adversely affect embryonic development during the pre-implantation period. As such, this not only reflects that PHLDA2 has dosage sensitive functions, but that it also may be a key gene controlling early embryonic development in the bovine embryo.

Association of Expression Levels of Imprinted Genes with Embryo Development

Genes showing higher expression in degenerate embryos appear to have roles critical for cell division. MKRN3 putatively functions as a ribonucleoprotein and been shown to be solely expressed after the maternal embryonic transition in bovine in-vitro embryos, where maternal stores of RNA are degraded and the embryonic transcripts have gained control [28, 29]. For PEG3, although its biological functions are still being determined, studies suggest a Peg3/PAX-1 mediation of p53-mediated cell apoptosis [30]. Our results may be indicative of increased cell death and lack of RNA modification in the degenerate embryos and may give rise to suggested roles in the embryo's developmental potential. Furthermore, UBE3A encodes for the E6-associated protein, which has a role as an ubiquitin ligase enzyme [31]. This is of interest as over-expression of this gene in degenerate embryos may result in an excess of polyubquitination and subsequent degradation of critical proteins by the proteosomes.

Of those genes found to have higher expression in blastocysts, reported functions are more limited. Studies suggest that IGF2R should be maintained at sufficient levels for proper development in utero [32]. In addition, low levels of IGF2R may result in developmental abnormalities such as large offspring syndrome [33]. Tssc4 has been mapped to a region on chromosome 7 in the mouse that has association with early embryonic lethality (http://www.mousebook.org/index.php), but there is little known regarding its function in cattle.

Four genes (USP29, NNAT, PEG10, and RTL1) had very low expression in embryos making it unable to quantify differences accurately, while three genes (IGF2, H19, and MIM1) had undetectable levels of expression in our embryo populations. This may be due to expression levels being below detection limits or an absence of transcripts due to no expression of these genes during this developmental period. Although there is some evidence for expression of H19 in mouse blastocysts [34], previous studies have shown that neither H19 nor IGF2 is expressed in bovine [5, 35] or ovine [36] blastocysts. One gene, XIST, was inconclusive in results due to sex bias as relative abundance for this gene has been shown to be higher in female blastocysts [37]. Thus, the use of pooling does not allow us to quantify this gene further.

An increasing number of studies have shown the importance and sensitivity of imprinted gene expression during the early developmental stages. A study by Tunster et al. [38] showed that a doubling of Phlda2 expression in mice resulted in a 25-35% reduction in embryonic glycogen stores and a 13% decrease in embryonic weight. Furthermore, another study revealed that Mash2-deficient mouse embryos died due to placental failure by Day 10 postcoitum [39]. A prior study in mice revealed 26 imprinted genes aberrantly expressed in abnormally developed placentas [40]. Interestingly, all of these genes showed a 3-fold or less change in expression suggesting a heightened sensitivity of the organism to deviations from normal imprinted gene expression. As such, the relatively small fold changes found in this study could still hold biological importance when it comes to the functions of imprinted genes.

Knockdown of CDKN1C Causes Reduced Blastocyst Development

CDKN1C ($p57^{KIP2}$) is a member of the CIP/KIP family of cell-cycle inhibitors that have unique roles in embryogenesis [41]. Although the primary role of CDKN1C is cell cycle regulation, it has also been implicated to have roles that in apoptosis, cytoskeletal dynamics, and differentiation [42]. Mice lacking Cdkn1c have been found to have increased neonatal lethality and those surviving showed numerous developmental abnormalities ranging from cleft palates to abdominal defects [43]. Another study showed that most mice devoid of Cdkn1c expression died after birth, and tissues of these individuals had an increase in apoptotic cells and signs of delayed differentiation [44]. In contrast, excess of this gene has been shown to have association with increased embryonic lethality, suggesting dosage sensitivity during early developmental stages [45]. We hypothesized that by knocking down expression of CDKN1C using siRNA, embryonic development would be negatively affected, as the gene showed lower expression levels in degenerated embryos compared to blastocysts.

Knockdown of CDKN1C in the bovine pre-implantation embryo resulted in a 45% decrease in blastocyst rate by day 8 of culture. Validation of knockdown was observed using qRT-PCR showing a 50% reduction in CDKN1C levels in day 8 blastocysts in comparison to sham and control groups. No significant effects were seen on cleavage rates. Given that CDKN1C knockdown resulted in reduced blastocyst formation suggests that this gene is a key factor driving early development. Specifically, these results imply that the differential expression that was observed between blastocyst and degenerates was causative, in part, to the embryos' degeneration.

Sensitivity of the Embryo to CDKN1C Dosage

Early embryonic development in mice has been shown to be extremely sensitive to the levels of Cdkn1c [45]. One excess copy caused growth retardation by E13.5 while loss of Cdkn1c resulted in overgrowth phenotypes [45]. Prior to differentiation into a blastocyst, individual blastomeres are totipotent; however, with differentiation the ICM cells gain pluripotentcy [46]. A study by Tury et al. [47] showed that Cdkn1c overexpression at E14.5-15.5 in mice resulted in a transition from proliferation to differentiation in neuronal tissues, whereas deficiency of this gene resulted in an opposite effect. Thus, a particular level of CDKN1C is required for proliferation to occur and then an increase in CDKN1C levels is required for a transition from cell division to differentiation. Indeed in our system there seems to be an apparent sensitivity to CDKN1C levels. Although cleavage rates were unaffected by knockdown, later development to the blastocyst stage was reduced significantly. This suggests that even low levels of CDKN1C were sufficient for early cell division but heightened levels may be needed for the transition to differentiation.

Individual Genes and Pathways Perturbed by CDKN1C Knockdown

A total of 51 genes showed significant differential expression between sham- and siRNA-injected embryos. Notably, functions of the 20 differentially-expressed genes with the greatest differences (>10-fold expression difference between embryo groups) included 10 genes involved in apoptosis (IFI6, IFI27, CCDC80, LUM, PHACTR3, GJA1, OLR1, CSRP3, NIM, and BMP2). For example, BMP2 can induce apoptosis by causing cell cycle arrest [48] and LUM may influence apoptosis through pathways regulated by Fas-Fas ligand interaction [49]. However, in addition to the functions of IFI6 and IFI27 in apoptosis, roles in viral infections have also been suggested [50]. Interestingly, the RNAi pathway in the cell can be induced by viral infection. Therefore, these two genes' expression levels may be increased in the siRNA-injected group due to the CDKN1C siRNA introduction. All the apoptotic genes were highly expressed in injected compared to non-injected embryos probably as a result of the apoptotic activity in the injected embryos. Other functions of the genes found to be altered as a consequence of siRNA injection include lipid metabolism (OLR1, FAT1, PLSCR1, and PARRES2), differentiation (CSRP3, CDH2, and BMP2), and cell cycle regulation (C27H8orf4). Thus, knockdown of CDKN1C identified many genes that are regulated by this gene with a wide range of functions essential to the developing embryo.

Of the nine significant pathways found in the GO analysis, the endonuclease activity pathway was enriched with genes that showed higher expression in sham than in injected embryos. Decreased endonuclease activity has been shown to associate with increased DNA damage in neuronal development [51]. It has been shown that ablation of certain genes involved in DNA damage repair in murine embryos leads to embryonic lethality [52]. Decreased ribonuclease activity in CDKN1C knockdown embryos may be causing increased cellular damage and reduced development. Thus, p57 (the protein product for CDKN1C) may be a responder for DNA damage in the cell, and inadequate levels may prevent the embryo from recovering from potentially fatal replication mistakes. In addition, it appears that metabolic processes in the siRNA-injected embryos are altered in comparison to shams.

Seven out of eight differentially expressed genes (ENO1, ENO3, GPI, PFKL, TPI1, DHDH, GALE) for monosaccharide catabolic process were found to be significantly higher in sham embryos. Interestingly, ENO1 and ENO3 code for enolase, which is one of the last steps in glycolysis [53]. Glycolysis, which is a redox reaction, is a pathway that derives adenosine triphosphate (ATP), a main source of energy in the cell. It has been suggested that shifts in redox reactions can affect cell activities post-compaction and at differentiation, which are two critical processes in the bovine pre-implantation embryo [54]. In addition, enolase may serve as a receptor for ligands on the surface of the cell [55]. This is intriguing as the extracellular region pathway was also enriched for differentially expressed genes in this study. During the transition from morula to blastocyst, cells of the pre-implantation embryo undergo numerous changes including differentiation into specific cell types. Although there are numerous hypotheses regarding the mechanism of cell fate and differentiation during this time, cell signaling has been suggested as a key component [56]. Early studies have suggested that CDK inhibitors have functional roles in extracellular signaling and as such, reduction of CDKN1C may be altering factors on the cellular membrane responsible for cell signaling [57]. Thus, reducing the level of CDKN1C and preventing protein production via RNAi leads to global changes in the bovine pre-implantation embryo and uncovers new genes and pathways regulated by this gene beyond its immediate responsibilities in the cell cycle.

These are nothing more than speculations about the potential functions of the genes affected by siRNA injection that inhibit the expression of the two genes. Probably we should delete them or bury them at the end of the examples.

CONCLUSIONS

Ten imprinted genes were found to be differentially expressed between blastocyst and degenerate embryos, among which PHLDA2 showed a higher expression level in degenerates than blastocysts and CDKN1C showed a higher expression level in blastocysts compared to degenerates. Knockdown of PHLDA2 and CDKN1C—which are located in the same gene cluster—resulted in significant changes in embryo development using gene-specific siRNA injection into one-cell zygotes. RNA-Seq transcriptomic analysis of CDKN1C-siRNA injected vs. non-injected embryos revealed many genes and pathways that may be regulated by CDKN1C with functions critical to developing embryo. This suggests that CDKN1C and PHLDA2 are major contributors to bovine embryo development.

REFERENCES

1. Farin P W, Piedrahita J A, Farin C E: Errors in development of fetuses and placentas from in vitro-produced bovine embryos. *Theriogenology* 2006, 65(1):178-191.
2. Khatib H, Monson R L, Schutzkus V, Kohl D M, Rosa G J M, Rutledge J J: Mutations in the STAT5A gene are associated with embryonic survival and milk composition in cattle. *Journal of Dairy Science* 2008, 91(2):784-793.
3. Huang W, Khatib H: Comparison of transcriptomic landscapes of bovine embryos using RNA-Seq. *Bmc Genomics* 2010, 11:711.
4. Huang W, Kirkpatrick B W, Rosa G J M, Khatib H: A genome-wide association study using selective DNA pooling identifies candidate markers for fertility in Holstein cattle. *Animal Genetics* 2010, 41(6):570-578.

5. Huang W, Yandell B S, Khatib H: Transcriptomic profiling of bovine IVF embryos revealed candidate genes and pathways involved in early embryonic development. *Bmc Genomics* 2010, 11.
6. Khatib H, Huang W, Wang X, Tran A H, Bindrim A B, Schutzkus V, Monson R L, Yandell B S: Single gene and gene interaction effects on fertilization and embryonic survival rates in cattle. *Journal of Dairy Science* 2009, 92(5):2238-2247.
7. Driver A M, Huang W, Gajic S, Monson R L, Rosa G J M, Khatib H: Short communication: Effects of the progesterone receptor variants on fertility traits in cattle. *Journal of Dairy Science* 2009, 92(8):4082-4085.
8. Bressan F F, De Bern T H C, Perecin F, Lopes F L, Ambrosio C E, Meirelles F V, Miglino M A: Unearthing the Roles of Imprinted Genes in the Placenta. *Placenta* 2009, 30(10):823-834.
9. Lefebvre L, Viville S, Barton S C, Ishino F, Keverne E B, Surani M A: Abnormal maternal behaviour and growth retardation associated with loss of the imprinted gene Mest. *Nature Genetics* 1998, 20(2):163-169.
10. Ono R, Nakamura K, Inoue K, Naruse M, Usami T, Wakisaka-Saito N, Hino T, Suzuki-Migishima R, Ogonuki N, Miki H et al: Deletion of Peg10, an imprinted gene acquired from a retrotransposon, causes early embryonic lethality. *Nature Genetics* 2006, 38(1):101-106.
11. Yang L, Chavatte-Palmer P, Kubota C, O'Neill M, Hoagland T, Renard J P, Taneja M, Yang X Z, Tian X C: Expression of imprinted genes is aberrant in deceased newborn cloned calves and relatively normal in surviving adult clones. *Molecular Reproduction and Development* 2005, 71(4):431-438.
12. Liu J H, Yin S, Xiong B, Hou Y, Chen D Y, Sun Q Y: Aberrant DNA methylation imprints in aborted bovine clones. *Molecular Reproduction and Development* 2008, 75(4):598-607.
13. Fire A, Xu S Q, Montgomery M K, Kostas S A, Driver S E, Mello C C: Potent and specific genetic interference by double-stranded RNA in *Caenorhabditis elegans*. *Nature* 1998, 391(6669):806-811.
14. Manrique C, Compan V, Rosselet C, Duflo S G D: Specific knock-down of GAD67 in the striatum using naked small interfering RNAs. *Journal of Biotechnology* 2009, 142(3-4):185-192.
15. Nganvongpanit K, Muller H, Rings F, Hoelker M, Jennen D, Tholen E, Havlicek V, Besenfelder U, Schellander K, Tesfaye D: Selective degradation of maternal and embryonic transcripts in in vitro produced bovine oocytes and embryos using sequence specific double-stranded RNA. *Reproduction* 2006, 131(5):861-874.
16. Lee K B, Bettegowda A, Wee G, Ireland J J, Smith G W: Molecular Determinants of Oocyte Competence: Potential Functional Role for Maternal (Oocyte-Derived) Follistatin in Promoting Bovine Early Embryogenesis. *Endocrinology* 2009, 150(5):2463-2471
17. Tesfaye D, Regassa A, Rings F, GhanemN, Phatsara C, Tholen E, Herwig R, Un C, Schellander K, Hoelker M: Suppression of the transcription factor MSX1 gene delays bovine preimplantation embryo development in vitro. *Reproduction* 2010, 139(5):857-870.
18. Tripurani S K, Lee K B, Wang L, Wee G, Smith G W, Lee Y S, Latham K E, Yao J B: A Novel Functional Role for the Oocyte-Specific Transcription Factor Newborn Ovary Homeobox (NOBOX) during Early Embryonic Development in Cattle. *Endocrinology* 2011, 152(3):1013-1023.
19. O'Meara C M, Murray J D, Mamo S, Gallagher E, Roche J, Lonergan P: Gene silencing in bovine zygotes: siRNA transfection versus microinjection. *Reproduction Fertility and Development* 2011, 23(4):534-543.
20. Jones P A, Takai D: The role of DNA methylation in mammalian epigenetics. *Science* 2001, 293(5532):1068-1070.
21. Hellman A, Chess A: Gene body-specific methylation on the active X chromosome. *Science* 2007, 315(5815):1141-1143.
22. Ball M P, Li J B, Gao Y, Lee J H, LeProust E M, Park I H, Xie B, Daley G Q, Church G M: Targeted and genome-scale strategies reveal gene-body methylation signatures in human cells. *Nature Biotechnology* 2009, 27(4):361-368.
23. Jjingo D, Conley A B, Yi S V, Lunyak V V, Jordan I K: On the presence and role of human gene-body DNA methylation. *Oncotarget* 2012, 3(4):462-474.
24. Sartori R, Sartor-Bergfelt R, Mertens S A, Guenther J N, Parrish J J, Wiltbank M C: Fertilization and early embryonic development in heifers and lactating cows in summer and lactating and dry cows in winter. *Journal of Dairy Science* 2002, 85(11):2803-2812.
25. Schrock G E, Saxton A M, Schrick F N, Edwards J L: Early in vitro fertilization improves development of bovine ova heat stressed during in vitro maturation. *Journal of Dairy Science* 2007, 90(9):4297-4303.
26. Hansen P J: Exploitation of genetic and physiological determinants of embryonic resistance to elevated temperature to improve embryonic survival in dairy cattle during heat stress. *Theriogenology* 2007, 68: S242-S249.
27. Roth Z, Hansen P J: Involvement of apoptosis in disruption of developmental competence of bovine oocytes by heat shock during maturation. *Biology of Reproduction* 2004, 71(6):1898-1906.
28. Jong M T C, Gray T A, Ji Y G, Glenn C C, Saitoh S, Driscoll D J, Nicholls R D: A novel imprinted gene, encoding a RING zinc-finger protein, and overlapping antisense transcript in the Prader-Willi syndrome critical region. *Human Molecular Genetics* 1999, 8(5):783-793.
29. Tveden-Nyborg P Y, Alexopoulos N I, Cooney M A, French A J, Tecirlioglu R T, Holland M K, Thomsen P D, D'Cruz N T: Analysis of the expression of putatively imprinted genes in bovine peri-implantation embryos. *Theriogenology* 2008, 70(7):1119-1128.
30. Deng Y B, Wu X W: Peg3/Pw1 promotes p53-mediated apoptosis by inducing Bax translocation from cytosol to mitochondria. *Proceedings of the National Academy of Sciences of the United States of America* 2000, 97(22): 12050-12055.
31. Williams C A: Neurological aspects of the Angelman syndrome. *Brain & Development* 2005, 27(2):88-94.
32. Gicquel C, Le Bouc Y: Hormonal regulation of fetal growth. *Hormone Research* 2006, 65:28-33.
33. Suteevun-Phermthai T, Curchoe C L, Evans A C, Boland E, Rizos D, Fair T, Duffy P, Sung L Y, Du F, Chaubal S et al: Allelic switching of the imprinted IGF2R gene in cloned bovine fetuses and calves. *Animal Reproduction Science* 2009, 116(1-2):19-27.
34. Fauque P, Jouannet P, Lesaffre C, Ripoche M A, Dandolo L, Vaiman D, Jammes H: Assisted reproductive technology affects developmental kinetics, H19 imprinting control region methylation and H19 gene expression in individual mouse. *Bmc Developmental Biology* 2007, 7.

35. Kues W A, Sudheer S, Herrmann D, Carnwath J W, Havlicek V, Besenfelder U, Lehrach H, Adjaye J, Niemann H: Genome-wide expression profiling reveals distinct clusters of transcriptional regulation during bovine preimplantation development in vivo (vol 105, pg 19768, 2008). *Proceedings of the National Academy of Sciences of the U.S. Pat. No.* 2,009,106(5):1679-1679.
36. Thurston A, Taylor J, Gardner J, Sinclair K D, Young L E: Monoallelic expression of nine imprinted genes in the sheep embryo occurs after the blastocyst stage. *Reproduction* 2008, 135(1):29-40.
37. Morton K M, Herrmann D, Sieg B, Struckmann C, Maxwell W M C, Rath D, Evans G, Lucas-Hahn A, Niemann H, Wrenzycki C: Altered mRNA expression patterns in bovine blastocysts after fertilisation in vitro using flow-cytometrically sex-sorted sperm. *Molecular Reproduction and Development* 2007, 74(8):931-940.
38. Tunster S J, Tycko B, John R M: The Imprinted Phlda2 Gene Regulates Extraembryonic Energy Stores. *Molecular and Cellular Biology* 2010, 30(1):295-306.
39. Guillemot F, Caspary T, Tilghman S M, Copeland N G, Gilbert D J, Jenkins N A, Anderson D J, Joyner A L, Rossant J, Nagy A: GENOMIC IMPRINTING OF MASH2, A MOUSE GENE REQUIRED FOR TROPHOBLAST DEVELOPMENT. *Nature Genetics* 1995, 9(3):235-242.
40. Bobetsis Y A, Barros S P, Lin D M, Arce R M, Offenbacher S: Altered gene expression in murine placentas in an infection-induced intrauterine growth restriction model: a microarray analysis. *Journal of Reproductive Immunology* 2010, 85(2):140-148.
41. Pateras I S, Apostolopoulou K, Niforou K, Kotsinas A, Gorgoulis V G: p57(KIP2): "Kip"ing the Cell under Control. *Molecular Cancer Research* 2009, 7(12):1902-1919.
42. Besson A, Dowdy S F, Roberts J M: CDK inhibitors: Cell cycle regulators and beyond. *Developmental Cell* 2008, 14(2):159-169.
43. Zhang P M, Liegeois N J, Wong C, Finegold M, Hou H, Thompson J C, Silverman A, Harper J W, DePinho R A, Elledge S J: Altered cell differentiation and proliferation in mice lacking p57(KIP2) indicates a role in Beckwith-Wiedemann syndrome. *Nature* 1997, 387(6629):151-158.
44. Yan Y M, Lee M H, Massague J, Barbacid M: Ablation of the CDK inhibitor p57(Kip2) results in increased apoptosis and delayed differentiation during mouse development. *Genes & Development* 1997, 11(8):973-983.
45. Andrews S C, Wood M D, Tunster S J, Barton S C, Surani M A, John R M: Cdkn1c (p57(Kip2)) is the major regulator of embryonic growth within its imprinted domain on mouse distal chromosome 7. *Bmc Developmental Biology* 2007, 7.
46. Sudheer S, Adjaye J: Functional genomics of human pre-implantation development. *Briefings in functional genomics & proteomics* 2007, 6(2):120-132.
47. Tury A, Mairet-Coello G, DiCicco-Bloom E: The Cyclin-Dependent Kinase Inhibitor p57(Kip2) Regulates Cell Cycle Exit, Differentiation, and Migration of Embryonic Cerebral Cortical Precursors. *Cerebral Cortex* 2011, 21(8):1840-1856.
48. Kawamura C, Kizaki M, Ikeda Y: Bone morphogenetic protein (BMP)-2 induces apoptosis in human myeloma cells. *Leukemia & Lymphoma* 2002, 43(3):635-639.
49. Vij N, Roberts L, Joyce S, Chakravarti S: Lumican suppresses cell proliferation and aids Fas-Fas ligand mediated apoptosis: implications in the cornea. *Experimental Eye Research* 2004, 78(5):957-971.
50. Cheriyath V, Leaman D W, Borden E C: Emerging Roles of FAM14 Family Members (G1P3/ISG 6-16 and ISG12/IF127) in Innate Immunity and Cancer. *Journal of Interferon and Cytokine Research* 2011, 31(1):173-181.
51. Huang E, Qu D, Zhang Y, Venderova K, Haque M E, Rousseaux M W C, Slack R S, Woulfe J M, Park D S: The role of Cdk5-mediated apurinic/apyrimidinic endonuclease 1 phosphorylation in neuronal death. *Nature Cell Biology* 2010, 12(6):563-U100.
52. Chen C-H, Chu P-C, Lee L, Lien H-W, Lin T-L, Fan C-C, Chi P, Huang C-J, Chang M-S: Disruption of Murine mp29/Syf2/Ntc31 Gene Results in Embryonic Lethality with Aberrant Checkpoint Response. *Plos One* 2012, 7(3).
53. Stein M, Gabdoulline R R, Wade R C: Cross-species analysis of the glycolytic pathway by comparison of molecular interaction fields. *Molecular bioSystems* 2010, 6(1):152-164.
54. Harvey A J, Kind K L, Thompson J G: REDOX regulation of early embryo development. *Reproduction* 2002, 123(4):479-486.
55. Seweryn E, Pietkiewicz J, Szamborska A, Gamian A: Enolase on the surface of prokaryotic and eukaryotic cells is a receptor for human plasminogen. *Postepy higieny i medycyny doswiadczalnej (Online)* 2007, 61:672-682.
56. Sasaki H: Mechanisms of trophectoderm fate specification in preimplantation mouse development. *Development Growth & Differentiation* 2010, 52(3):263-273.
57. Polyak K, Lee M H, Erdjumentbromage H, Koff A, Roberts J M, Tempst P, Massague J: CLONING OF P27(KIP1), A CYCLIN-DEPENDENT KINASE INHIBITOR AND A POTENTIAL MEDIATOR OF EXTRACELLULAR ANTIMITOGENIC SIGNALS. *Cell* 1994, 78(1):59-66.
58. Vandesompele J, De Preter K, Pattyn F, Poppe B, Van Roy N, De Paepe A, Speleman F: Accurate normalization of real-time quantitative RT-PCR data by geometric averaging of multiple internal control genes. *Genome biology* 2002, 3(7):RESEARCH0034-RESEARCH0034.
59. Livak K J, Schmittgen T D: Analysis of relative gene expression data using real-time quantitative PCR and the 2(-Delta Delta C(T)) method. *Methods* 2001, 25(4):402-408.
60. Nykarien A, Haley B, Zamore P D: ATP requirements and small interfering RNA structure in the RNA interference pathway. *Cell* 2001, 107(3):309-321.
61. Driver A M, Penagaricano F, Huang W, Ahmad K R, Hackbart K S, Wiltbank M C, Khatib H: RNA-Seq analysis uncovers transcriptomic variations between morphologically similar in vivo- and in vitro-derived bovine blastocysts. *Bmc Genomics* 2012, 13.
62. Trapnell C, Pachter L, Salzberg S L: TopHat: discovering splice junctions with RNA-Seq. *Bioinformatics* 2009, 25(9):1105-1111.
63. Trapnell C, Williams B A, Pertea G, Mortazavi A, Kwan G, van Baren M J, Salzberg S L, Wold B J, Pachter L: Transcript assembly and quantification by RNA-Seq reveals unannotated transcripts and isoform switching during cell differentiation. *Nature Biotechnology* 2010, 28(5):511-U174.
64. Roberts A, Trapnell C, Donaghey J, Rinn J L, Pachter L: Improving RNA-Seq expression estimates by correcting for fragment bias. *Genome biology* 2011, 12(3).
65. Young M D, Wakefield M J, Smyth G K, Oshlack A: Gene ontology analysis for RNA-seq: accounting for selection bias. *Genome biology* 2010, 11(2).
66. Wee G, Koo D B, Song B S, Kim J S, Kang M J, Moon S J, Kang Y K, Lee K K, Han Y M: Inheritable histone H4 acetylation of somatic chromatins in cloned embryos. *Journal of Biological Chemistry* 2006, 281(9):6048-6057.

What is claimed is:

1. A method of improving the likelihood of a bovine embryo to develop successfully, the method comprising i) obtaining a supply of fertilized bovine eggs, ii) micro-injecting a suitable dosage of 5'-phospate-modified PHLDA2 siRNA into the fertilized bovine eggs, wherein blastocyst rate is increased compared to non-injected or sham injected controls; and iii) cultivating the fertilized eggs until they are ready for planting into a uterus.

2. The method of claim 1, wherein the 5'-phospate-modified PHLDA2 siRNA comprises a duplex of PHLDA2 antisense [Phos]AGUAGCACCGGGCUAUAUCdTdT (SEQ ID No. 1), and PHLDA2 Sense GAUAUAGCCCG-GUGCUACUdTdT (SEQ ID No. 2).

3. The method of claim 2, wherein about 100 μM of the 5'-phospate-modified PHLDA2 siRNA is injected per fertilized egg.

* * * * *